(12) United States Patent
Tagawa et al.

(10) Patent No.: US 9,885,661 B2
(45) Date of Patent: Feb. 6, 2018

(54) ANALYTE DETECTION METHOD, FLUORESCENCE DETECTION METHOD, AND FLUORESCENCE DETECTION APPARATUS USING SAME

(71) Applicant: Sysmex Corporation, Kobe-shi, Hyogo (JP)

(72) Inventors: Ayato Tagawa, Kobe (JP); Hiroya Kirimura, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 441 days.

(21) Appl. No.: 14/508,498

(22) Filed: Oct. 7, 2014

(65) Prior Publication Data

US 2015/0104880 A1    Apr. 16, 2015

(30) Foreign Application Priority Data

Oct. 10, 2013  (JP) ................................ 2013-212886
Sep. 11, 2014  (JP) ................................ 2014-184832

(51) Int. Cl.
*G01N 21/64*    (2006.01)
*G01N 33/53*    (2006.01)

(52) U.S. Cl.
CPC ....... *G01N 21/6486* (2013.01); *G01N 21/645* (2013.01); *G01N 33/5308* (2013.01); *G01N 21/6454* (2013.01); *G01N 2458/00* (2013.01)

(58) Field of Classification Search
CPC ............. G01N 21/6486; G01N 21/645; G01N 33/5308; G01N 21/6454; G01N 2458/00
See application file for complete search history.

(56) References Cited

U.S. PATENT DOCUMENTS

2012/0161268 A1   6/2012  Iwanaga et al.
2013/0157351 A1*  6/2013  Ozcan ................ G01N 21/6486
                                                      435/288.7

FOREIGN PATENT DOCUMENTS

EP    2 634 561 A1       9/2013
WO    WO 2007/008864 A2  1/2007
WO    WO 2010/148252 A1  12/2010

OTHER PUBLICATIONS

Dandin, M. et al., "Optical Filtering Technologies for Integrated Fluorescence Sensors", *Lab on a Chip*, vol. 7, No. 8, Jul. 10, 2007, pp. 995 (Abstract only; printed from the internet on Jul. 27, 2015).

(Continued)

*Primary Examiner* — Rebecca L Martinez
(74) *Attorney, Agent, or Firm* — Brinks Gilson & Lione

(57) ABSTRACT

Disclosed is an analyte detection method for detecting an analyte contained in a biological sample, constituted by irradiating a light of a first peak wavelength on a complex containing an analyte and fluorescent substance which gives off light of a second peak wavelength of 450 nm or higher but not exceeding 900 nm when irradiated with light of the first wavelength of 190 nm or higher but not exceeding 350 nm, detecting the light of the second peak wavelength given off by the fluorescent substance when irradiated by light of the first peak wavelength, by a photodetector, wherein the photodetector has a quantum efficiency in the second peak wavelength that is two or more times the quantum efficiency in the first peak wavelength.

18 Claims, 23 Drawing Sheets

(56) References Cited

OTHER PUBLICATIONS

Iordanov, V.P. et al, "Integrated Sensor Arrays for Bioluminescence and Fluorescence Bio-Chemical Analysis", Proceedings of IEEE Sensors 2004: [IEEE Sensors 2004 Conference], Oct. 24, 2004, pp. 810-813 (Abstract only; printed from the internet on Jul. 27, 2015).

Iordanov, V.P. et al, "Silicon Thin-Film UV Filter for NADH Fluorescence Analysis", *Sensors and Actuators,* vol. 97-98, Apr. 2002, pp. 161-166 (Abstract only; printed from the internet on Jul. 27, 2015).

Coskun, Ahmet F. et al., "Wide field-of-view lens-free fluorescent imaging on a chip," *Lab Chip,* Apr. 7, 2010, 10(7): 824-827, 10 pages.

Tagawa, Ayato et al., "Development of Complementary Metal Oxide Semiconductor Imaging Devices for Detecting Green Fluorescent Protein in the Deep Brain of a Freely Moving Mouse," *Japanese Journal of Applied Physics,* 48 (2009) 04C195, 2009, 5 pages.

\* cited by examiner

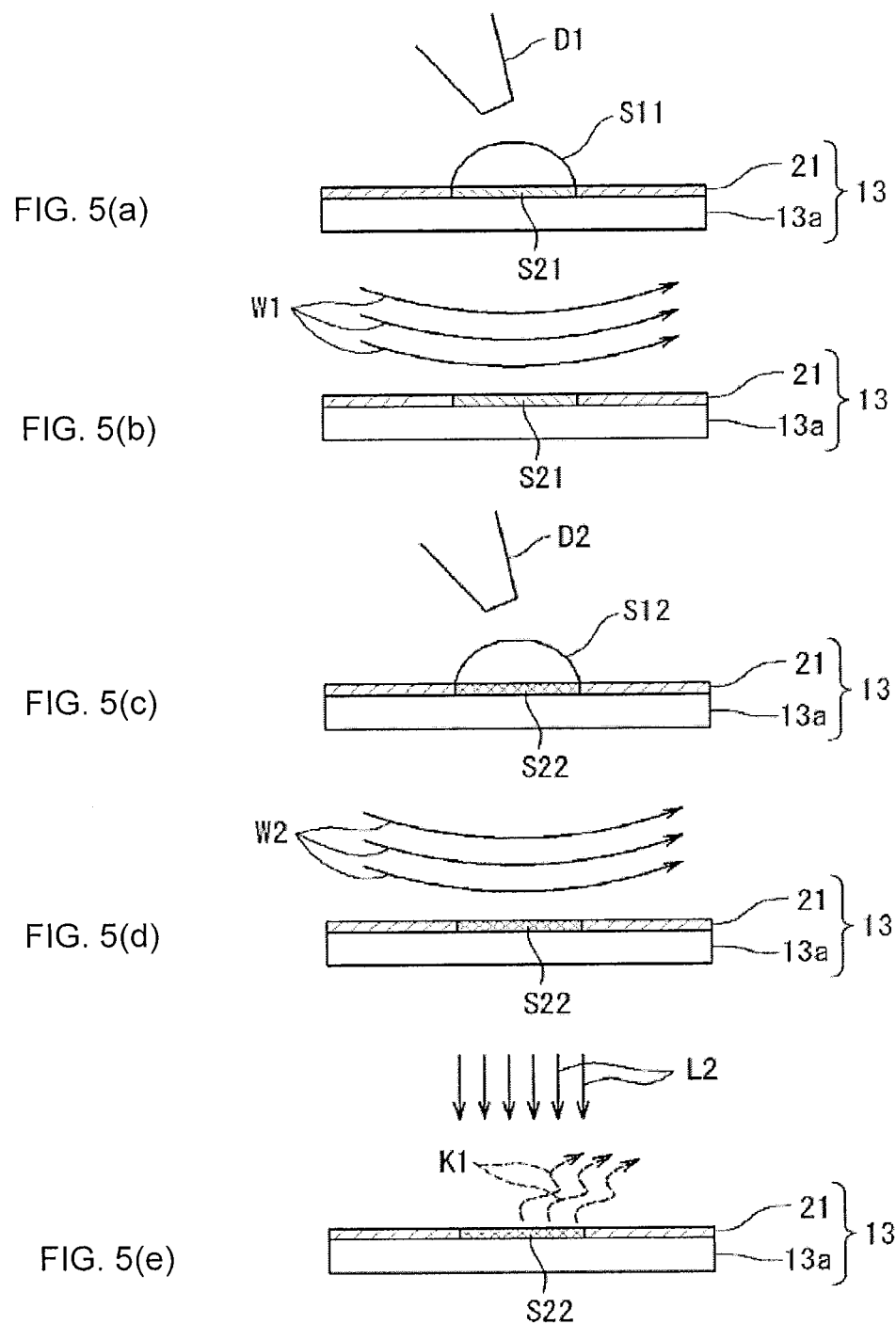

FIG. 6(a-1)    FIG. 6(a-2)    FIG. 6(a-3)
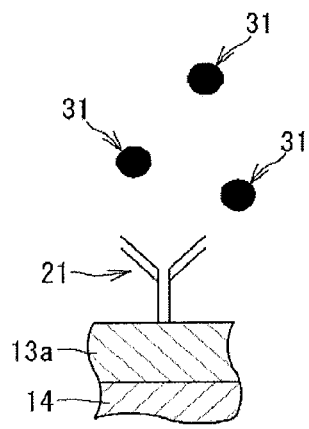 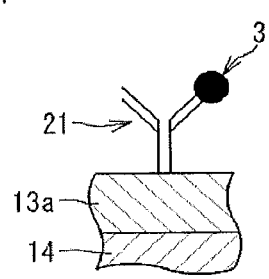 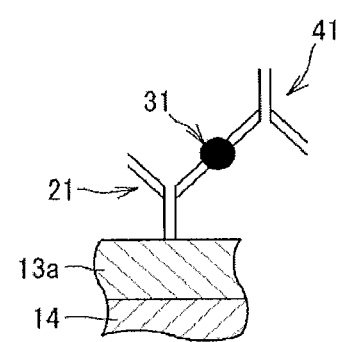
FIG. 6(b-1)    FIG. 6(b-2)
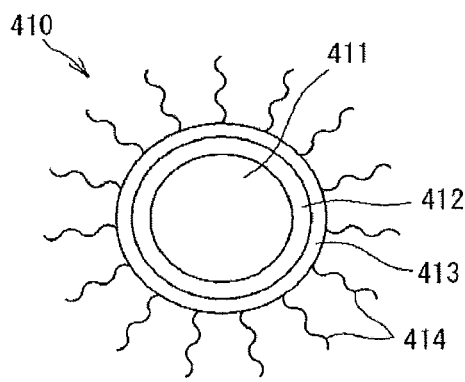 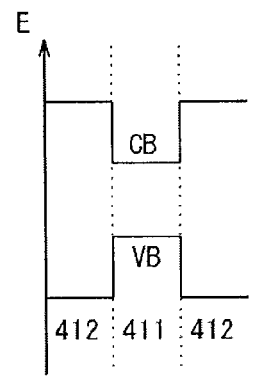

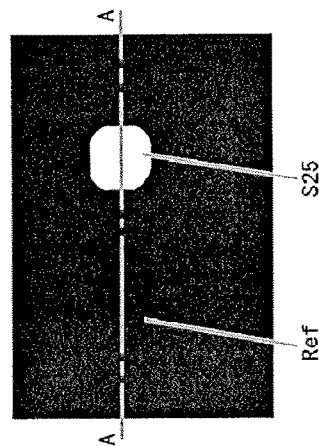
FIG. 16(a-1)
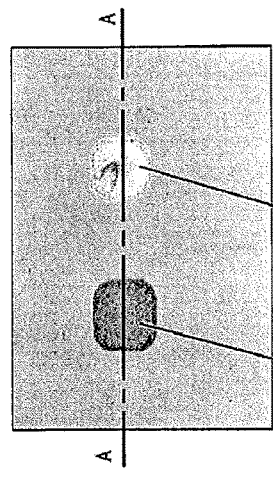
FIG. 16(b-1)
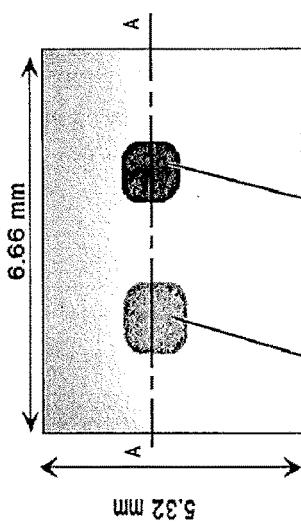
FIG. 16(c-1)
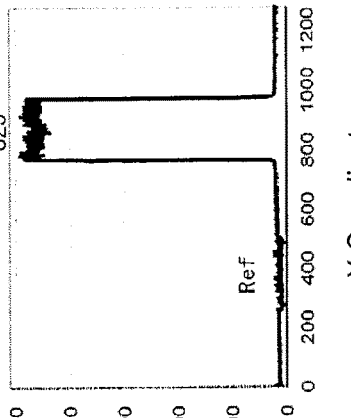
FIG. 16(a-2)
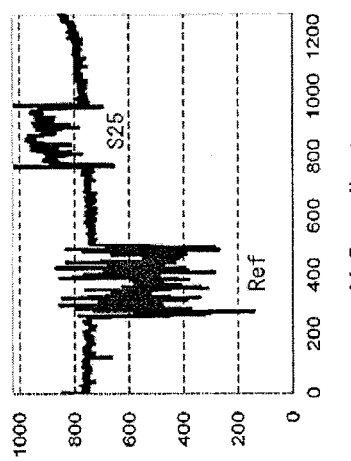
FIG. 16(b-2)
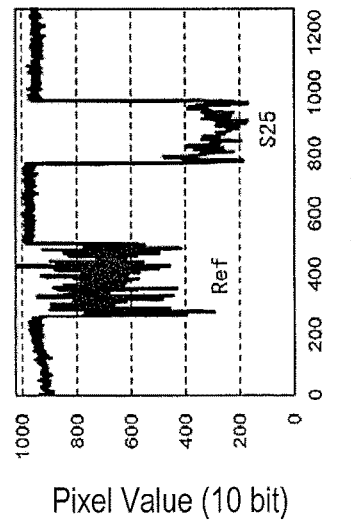
FIG. 16(c-2)

Bright-field Image
λ peak = 405 nm
Excitation
FIG. 19(a-2)  FIG. 19(a-1)
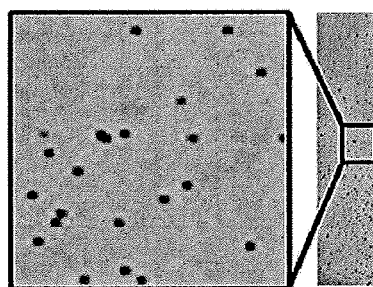
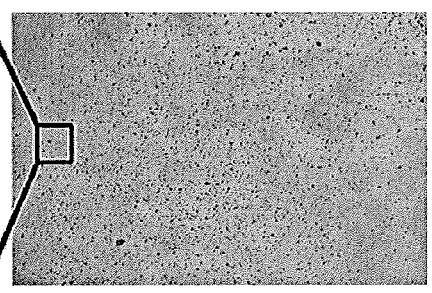
Fluorescent Image
λ peak = 270 nm
Excitation
FIG. 19(b-2)  FIG. 19(b-1)
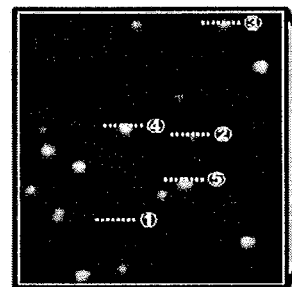
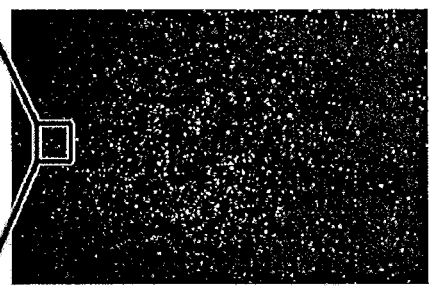

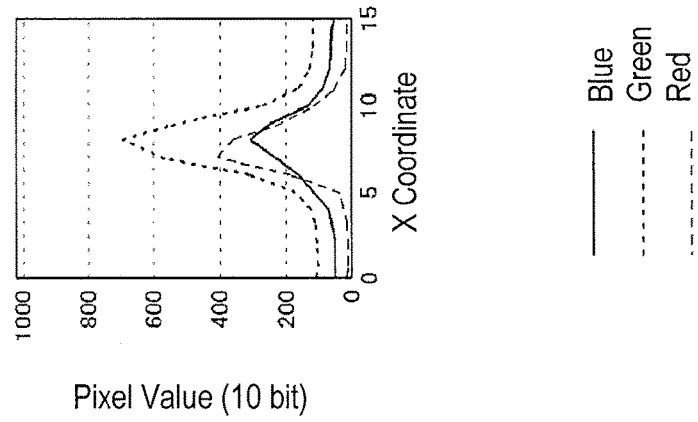
FIG. 20(1) Non-fluorescent light
FIG. 20(2) Wavelength 415 nm
FIG. 20(3) Wavelength 515 nm
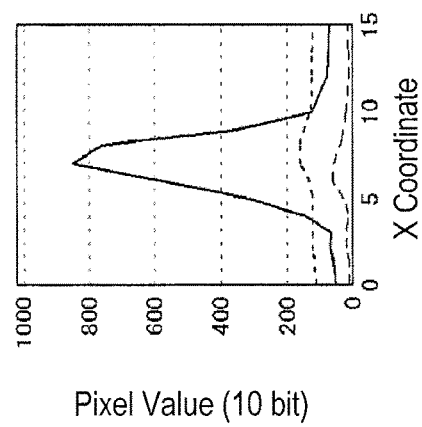
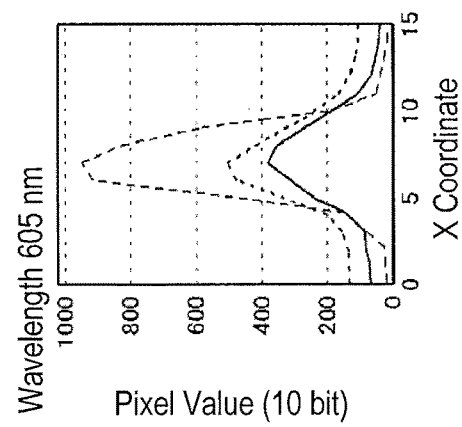
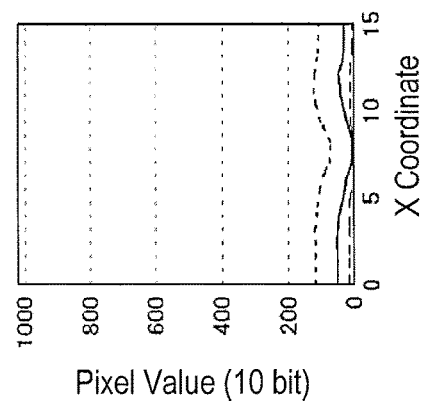
FIG. 20(4) Wavelength 565 nm
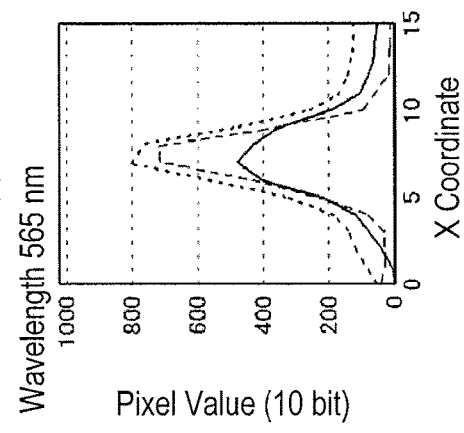
FIG. 20(5) Wavelength 605 nm

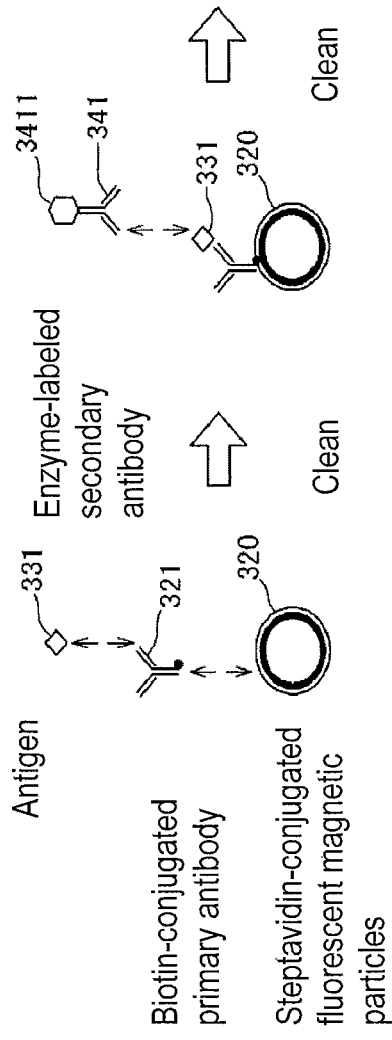

Negative Control (0 IU/mL HbsAg)   Positive Control (2500 IU/mL HbsAg)

ANALYTE DETECTION METHOD, FLUORESCENCE DETECTION METHOD, AND FLUORESCENCE DETECTION APPARATUS USING SAME

RELATED APPLICATIONS

This application claims priority under 35 U.S.C. §119 to Japanese Patent Application Nos. 2013-212886 filed on Oct. 10, 2013 and 2014-184832 filed on Sep. 11, 2014, the entire contents of which are hereby incorporated by reference.

FIELD OF THE INVENTION

The invention relates to an analyte detection method, fluorescence detection method, and analyte detection apparatus and fluorescence detection apparatus using same, and specifically relates to art for improving detection sensitivity.

BACKGROUND OF THE INVENTION

Analyte detection methods for detecting an analyte have been proposed which use a labeling substance for activation when irradiated with light as a method for detecting an analyte such as a gene, protein or the like contained in a biological sample (for example, refer to United States Patent Application Publication No. 2012/0161268).

Methods for detecting an analyte by detecting the light given off from a fluorescent substance when a labeling substance, that is, the fluorescent substance, bonded to the analyte is photo-excited are this type of analyte detection method. In this analyte detection method, a trace amount of analyte gives off weak light from the fluorescent substance bonded to the analyte. It is therefore important to improve the signal-to-noise (S/N) ratio of the detection signals output from the detection device in order to detect the light emitted from the fluorescent substance with high sensitivity.

SUMMARY OF THE INVENTION

The scope of the present invention is defined solely by the appended claims, and is not affected to any degree by the statements within this summary.

The analyte detection method of one aspect is an analyte detecting method for detecting an analyte contained in a biological sample, constituted by irradiating a light of a first peak wavelength on a complex containing an analyte and fluorescent substance which gives off light of a second peak wavelength of 450 nm or higher but not exceeding 900 nm when irradiated with light of the first peak wavelength of 190 nm or higher but not exceeding 350 nm, detecting the light of the second peak wavelength given off by the fluorescent substance when irradiated by light of the first peak wavelength, by a photodetector, wherein the photodetector has a quantum efficiency in the second peak wavelength that is two or more times the quantum efficiency in the first peak wavelength.

The analyte detection method of another aspect is an analyte detecting method for detecting an analyte contained in a biological sample, constituted by irradiating a light of a first peak wavelength on a complex containing an analyte and fluorescent substance which gives off light of a second peak wavelength of 450 nm or higher but not exceeding 900 nm when irradiated with light of the first wavelength 190 nm or higher but not exceeding 350 nm as a result of the reaction between the substrate and an enzyme in a complex containing the enzyme and an analyte, detecting the light of the second peak wavelength given off by the fluorescent substance when irradiated by light of the first peak wavelength, by a photodetector, wherein the photodetector has a quantum efficiency in the second peak wavelength that is two or more times the quantum efficiency in the first peak wavelength.

The fluorescence detection method of one aspect irradiates light of a first peak wavelength on a fluorescent substance which gives off light of a second peak wavelength of 450 nm or higher but not exceeding 900 nm when irradiated with light of the first wavelength of 190 nm or higher but not exceeding 350 nm, detects the light of the second peak wavelength given off by the fluorescent substance when irradiated by light of the first peak wavelength, by a photodetector, wherein the photodetector has a quantum efficiency in the second peak wavelength that is two or more times the quantum efficiency in the first peak wavelength.

The analyte detection apparatus of one aspect is an analyte detection apparatus for detecting an analyte contained in a biological sample, constituted by a light source for irradiating light of a first peak wavelength on a complex containing an analyte and fluorescent substance which gives off light of a second peak wavelength of 450 nm or higher but not exceeding 900 nm when irradiated with light of the first wavelength of 190 nm or higher but not exceeding 350 nm, and a photodetector for detecting the light of the second peak wavelength given off by the fluorescent substance when irradiated by light of the first peak wavelength emitted from the light source, wherein the photodetector has a quantum efficiency in the second peak wavelength that is two or more times the quantum efficiency in the first peak wavelength.

The analyte detection apparatus of another aspect is an analyte detection apparatus for detecting an analyte contained in a biological sample, constituted by a light source for irradiating light of a first peak wavelength on a fluorescent substance which gives off light of a second peak wavelength of 450 nm or higher but not exceeding 900 nm when irradiated with light of the first wavelength of 190 nm or higher but not exceeding 350 nm as a result of the reaction between the substrate and an enzyme in a complex containing the enzyme and an analyte, and a photodetector for detecting the light of the second peak wavelength given off by the fluorescent substance when irradiated by light of the first peak wavelength, wherein the photodetector has a quantum efficiency in the second peak wavelength that is two or more times the quantum efficiency in the first peak wavelength.

The fluorescence detection apparatus of yet another aspect constitutes a light source for irradiating light of a first peak wavelength on a fluorescent substance which gives off light of a second peak wavelength of 450 nm or higher but not exceeding 900 nm when irradiated with light of the first wavelength of 190 nm or higher but not exceeding 350 nm, and a photodetector for detecting the light of the second peak wavelength given off by the fluorescent substance when irradiated by light of the first peak wavelength, wherein the photodetector has a quantum efficiency in the second peak wavelength that is two or more times the quantum efficiency in the first peak wavelength.

BRIEF DESCRIPTION OF THE DRAWINGS

FIGS. 5(a) through 5(e) schematically illustrate the processing sequence of the analyte detection method of the first embodiment;

FIGS. 6(a-1) through 6(a-3) schematically show the processing sequence of the analyte detection method of the first embodiment, FIG. 6(b-1) shows the structure of the quantum dots of the first embodiment, and FIG. 6(b-2) is a band diagram of the quantum dots of the first embodiment;

FIG. 16(a-1) is an image obtained by a comparative example 1, FIG. 16(b-1) is an image obtained by a comparative example 2, and FIG. 16(c-1) is an image obtained by example 1; FIG. 16(a-2) shows intensity profile at the A-A line of FIG. 16(a-1), FIG. 16(b-2) shows the intensity profile at the A-A line of FIG. 16(b-1), and FIG. 16(c-2) shows the intensity profile at the A-A line of FIG. 16(c-1);

FIGS. 19(a-1) and 19(a-2) are bright-field images obtained by comparative example 3, and FIGS. 19(b-1) and 19(b-2) are the fluorescent images of same;

FIGS. 20(1) through 20(5) show the intensity profile of the fluorescent image shown in FIGS. 19(b-1) and 19(b-2);

FIGS. 21(I) through 21(III) show the procedure of generating the complex containing the analyte used in comparative example 4;

DETAILED DESCRIPTION OF THE PREFERRED EMBODIMENTS

First Embodiment

<1> Structure

Figure 1:
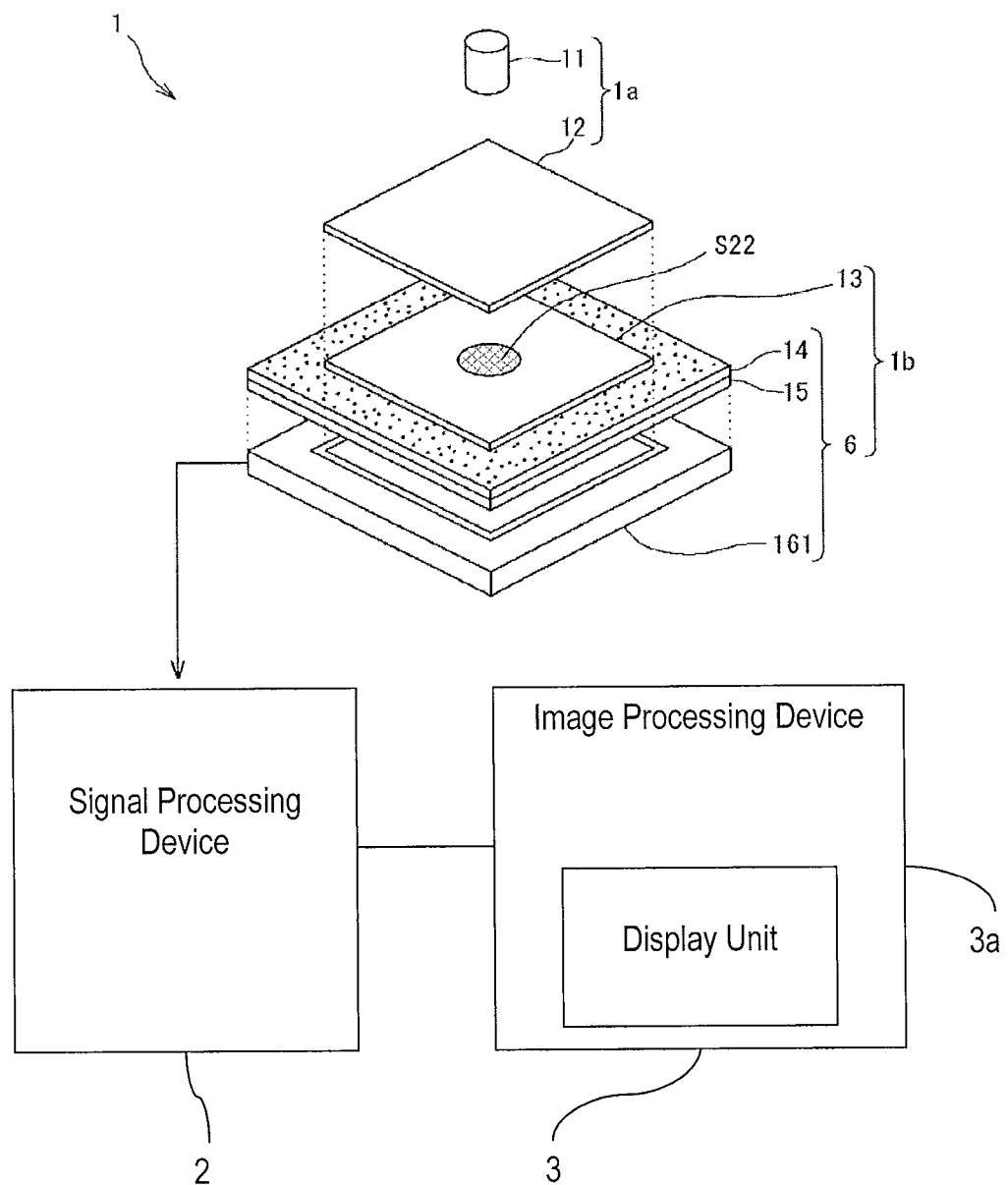
FIG. 1 is a brief structural view of the analyte detection system of a first embodiment.

The structure of the analyte detection system of the first embodiment is described below. The analyte detection system has an analyte detection apparatus 1, signal conversion device 2, and image processing device 3.

The analyte detection apparatus 1 has a light source 11, light diffusing member 12, analyte holding part 13, and photodetector 6. The light source 11, light diffusing member 12, analyte holding part 13, and photodetector 6 are respectively overlaid in this order. The light diffusing member 12 is arranged on the light source 11 side in the analyte holding part 13. The analyte detection apparatus 1 is configured by a first unit 1a which includes the light source 11 and the light diffusing member 12, and a second unit 1b which includes the analyte holding part 13 and the photodetector 6. The photodetector 6 includes a photoreceptor 16 which is described later.

The light source 11 emits light of a first peak wavelength. The first peak wavelength is 270 nm in the first embodiment. A semiconductor light-emitting element such as an LED (light emitting diode) is used as the light source 11. Since the light source 11 is configured by a semiconductor light-emitting element such as an LED which has relatively low power consumption compared to a light bulb, it is possible to reduce the power consumption compared to configuration which uses a light bulb as the light source 11. When light is emitted by the light source 11, a complex containing a fluorescent substance and an analyte is present in the analyte holding part 13 in region S22. When region S22 is irradiated by the light from the light source 11, the fluorescent substance in the complex undergoes photoexcitation. The fluorescent substance gives off light of a second peak wavelength which is different from the first peak wavelength when the fluorescent substance is excited via the light of the first peak wavelength. The second peak wavelength is 705 nm in the first embodiment. Quantum dots are used as the fluorescent substance. Note that quantum dots are described in detail below in section <3>.

The light diffusing member 12 functions to diffuse the light emitted from the light source 11. For example, a member having a dispersion of transparent particles which have a different refractive index than the base material in a transparent base, or transparent base material subjected to a surface blasting process may be used as the light diffusing member 12. As indicated by the arrows L1 in FIG. 2, the light from the light source 11 impinging the surface of the light diffusing member 12 which is facing the light source 11 is diffused in directions perpendicular to the thickness direction of the light diffusing member 12, and emerges from the opposite side of the diffusing member 12 to the side facing the light source 11 as indicated by the arrows L2 in FIG. 2.

Figure 2:
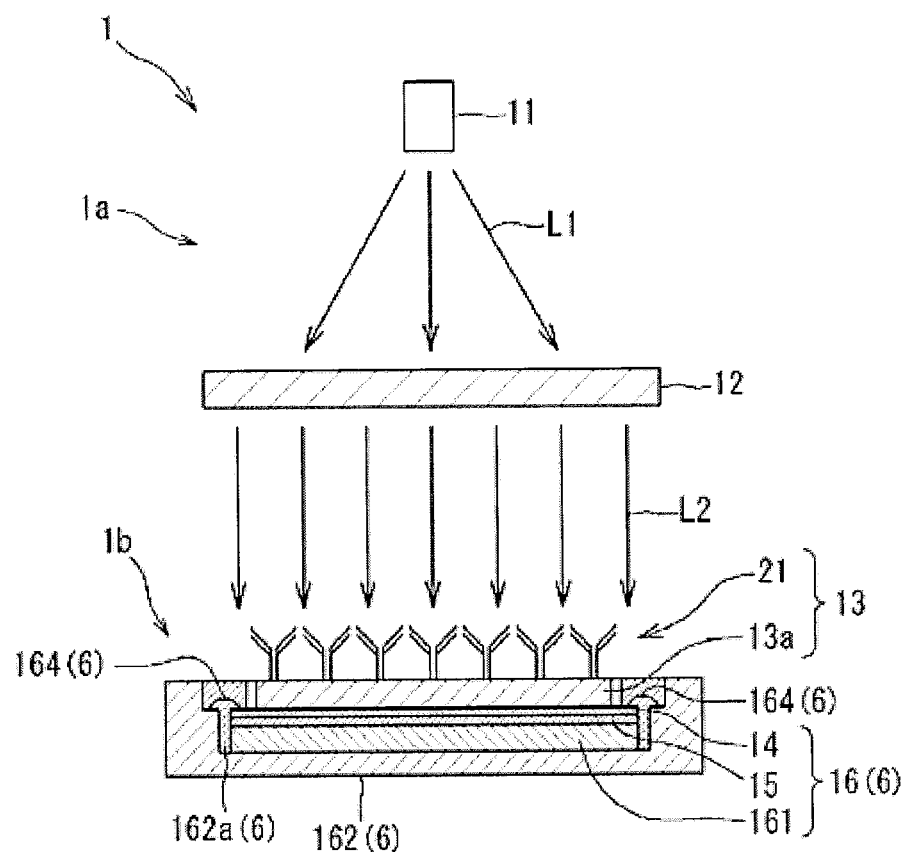
FIG. 2 is a brief structural view of the analyte detection apparatus of the first embodiment viewed from the side.

As shown in FIG. 2, the analyte holding part 13 is configured by a base 13a, and a capture agent 21 immobilized on the surface of the base 13 on the side facing the light diffusing member 12. The analyte holding part 13 holds the analyte when the capture agent 21 has the analyte in a captured state.

The base 13a is a plate formed of transparent material, and is arranged so as to cover the photoelectric conversion element 161 of the photodetector 6 which is described later.

The capture agent 21 is immobilized on the side of the base 13a which faces the light diffusing member 12. Immobilization of the capture agent 21 on the base 13a may be accomplished through a linking group bonded to the base 13a. For example, a thiol group, a hydroxyl group, a phosphate group, a carboxyl group, a carbonyl group, an aldehyde group, a sulfonic acid group, amino group and the like may be used as the linking group. Immobilization of the capture agent 21 on the base 13a also may be accomplished by a physical absorption method or ion bonding method. The amount of capture agent immobilized on the base 13a is not specifically limited insofar as the amount is set in accordance with the application and purpose.

The capture agent 21 may be appropriately selected according to the type of analyte. For example, when the analyte is nucleic acid, a nucleic acid probe that hybridizes to the nucleic acid, an antibody to the nucleic acid, protein that bonds to the nucleic acid and the like may be used as the capture agent 21. When the analyte is a protein or peptide, an antibody to the protein or peptide may be used as the capture agent 21. Thus, the analyte holding part 13 can selectively hold an organic substance specifically corresponding to the capture agent 21. It is therefore possible to remove only the analyte from the sample containing a mixture of an analyte and other contaminants.

The capture of the analyte by the capture agent 21 may be accomplished, for example, under the condition of bonding the analyte to the capture agent 21. The condition of bonding the analyte to the capture agent 21 is appropriately selected according to the type of analyte. For example, when the analyte is nucleic acid and the capture agent 21 is a nucleic acid probe which hybridizes top the nucleic acid, the capture of the analyte can be accomplished in the presence of a hybridization buffer. Alternatively, when the analyte is nucleic acid and the capture agent 21 is an antibody to the nucleic acid, antibody to a protein, or antibody to a peptide, the capture of the analyte can be carried out in a solution which is suitable to effect antigen-antibody reaction in phosphate buffered saline, HEPES buffer, PIPES buffer, Tris buffer and the like. When the analyte is a ligand and the capture agent 21 is a receptor for the ligand, or the analyte is a receptor and the capture agent 21 is a ligand for the receptor, the capture of the analyte can be carried out in a solution that is suitable for binding the ligand to the receptor.

The photodetector 6 is mainly configured by a photoreceptor 16, support substrate 162, wire 164 which electrically connects the photoreceptor 16 and the support substrate 162, and a resin part 162a which is provided medially to the support substrate 162 and the photoreceptor 16.

The photoreceptor 16 has a first protective layer 14, second protective layer 15, and photoelectric conversion element 161. The first protective layer 14 is superimposed on the second protective layer 15, and the second protective layer 15 is superimposed on the photoelectric conversion element 161. The first protective layer 14, second protective layer 15, and photoelectric conversion element 161 are integratedly formed as a unit.

Figure 3:
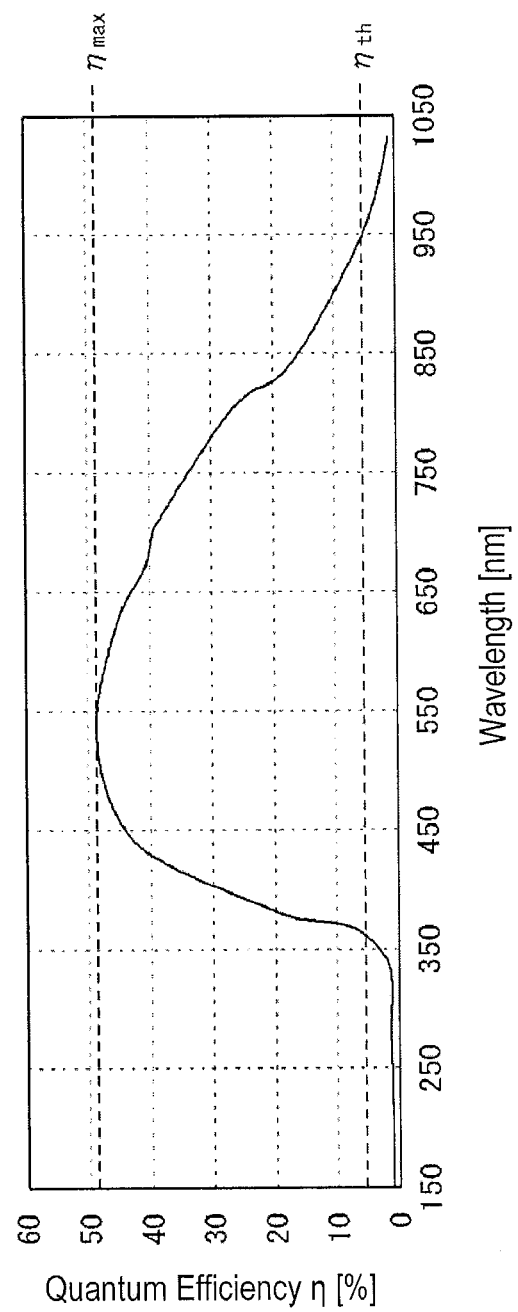
FIG. 3 is an illustration of the sensitivity characteristics of the photodetector of the first embodiment.

The photodetector 6 has the sensitivity characteristics shown in FIG. 3. In the first embodiment, the photodetector 6 is a sensor which uses the photoelectric conversion element that employs a silicon substrate in the photoreceptor 1, and more specifically, is a CMOS image sensor which uses a photodiode that employs the silicon substrate. The CMOS image sensor may be fabricated using a MOSFET and photodiode on a silicon substrate, and well known ion injection technique and film forming technique for wiring.

The CMOS image sensor has a structure of a plurality of cells (not shown in the drawing) configured by a photodiode and MOSFET connected to the photodiode, and the cells are arrayed in a grid pattern. Since the plurality of cells are integrated in the photodetector 6 the resolution of images captured by the photodetector 6 can be improved and therefore analyte detection sensitivity can be improved by using a solid state imaging device such as a CMOS image sensor. Since the CMOS image sensor has relatively low power consumption compared to PMT (photomultiplier tube), the photodetector has low power consumption compared to structures using PMT and the like.

The sensitivity characteristics of the photodetector 6 of the first embodiment are shown in FIG. 3. In FIG. 3, $\eta$ is the quantum efficiency of the photodetector 6, $\eta$max is the maximum value of the quantum efficiency, and $\eta$th is 5% quantum efficiency. The quantum efficiency maximum value $\eta$max includes the wavelength range 450 nm and higher but less than 900 nm. The photodetector 6 has approximately 0% quantum efficiency in the first peak wavelength, and 40% quantum efficiency in the second peak wavelength, and the quantum efficiency in the second peak wavelength is more than twice the quantum efficiency in the first peak wavelength.

The first protective layer 14 and the second protective layer 15 protect the photoelectric conversion element 161. The first protective layer 14 is configured by, for example, silicon nitride (SiN) film, and the second protective layer 15 is configured by silicon oxide (SiO2) film. The second protective layer 15 fulfills the role of reinforcing the first protective layer 14. A micro lens array configured by a plurality of micro lenses is provided on the analyte holding part 13 side of the first protective layer 14.

The photoelectric conversion element 161 is, for example, a photodiode using a silicon substrate. The light received by each cell of the photoelectric conversion element 161 is converted to a detection signal by the photodiode and sent to the support substrate side. The first protective layer 14 an individual micro lens provided at a position corresponding to each of the plurality of cells of the photoelectric conversion element 161. Pins for extracting the signal of each cell to the outside are provided on the periphery of the photoelectric conversion element 161.

The support substrate 162 supports the photoreceptor 16. The support substrate 162 is a silicon substrate, and has a recess formed in the center part, and a plurality of pins (not shown in the drawing) for extracting the signals to the periphery of the recess. The photoreceptor 16 is arranged in side this recessed part of the support substrate 162.

The wire 164 connects the pin provided on the periphery of the photoelectric conversion element 161 and the pin provided on the support substrate 162. The wire 164 is embedded within the resin part 162a.

The first unit 1a has, for example, a movable support member (not shown in the drawing) for supporting the light source 11, and a light source controller (not shown in the drawing) for controlling the intensity, direction, and position of the light emitted from the light source 11. The support member has a light source moving device for changing the direction and position of the light source 11.

Figure 4:
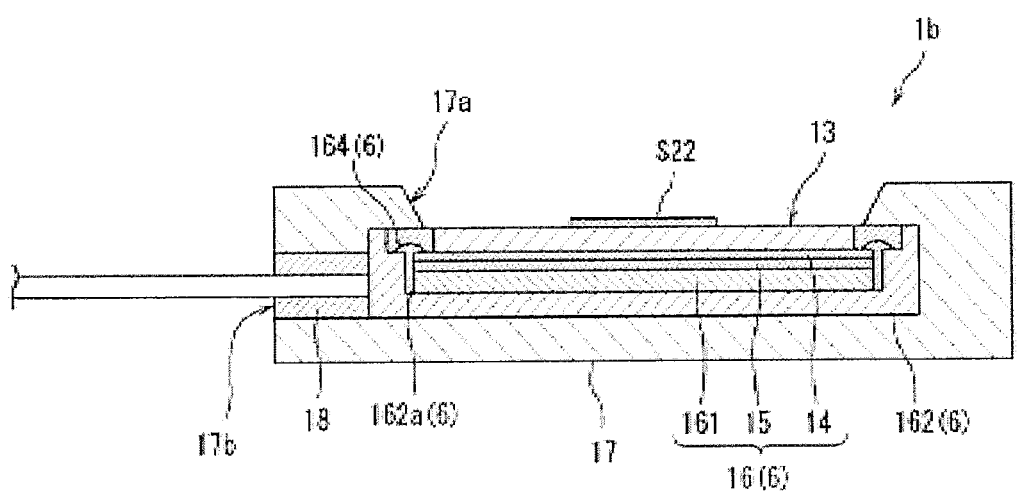
FIG. 4 is a brief cross sectional view of the second unit of the analyte detection apparatus of the first embodiment.

FIG. 4 is a brief cross sectional view of the second unit 1b of the analyte detection apparatus 1 of the first embodiment. As shown in FIG. 4, the second unit 1b has a housing 17 which houses the analyte holding part 13 and photodetector 6. The housing 17 is provided with a window 17a for taking in light to the photoreceptor 16 of the photodetector 6, and a signal line outlet hole 17b for letting out the signal line connected to the photoreceptor 16 to the outside. The window 17a of the housing 17 is covered by the analyte holding part 13. A waterproofing bushing 18 is provided medially to the outer surface of the signal line and the inner surface of the signal line outlet hole 17b of the housing 17.

The signal conversion device 2 converts the signals obtained from the photoelectric conversion element 16 to image information, and outputs the image information to the image processing device 3. The signal conversion device 2, for example, includes an analog-to-digital converter for converting the analog signals received from the photoelectric conversion element 16 to digital signals.

The image processing device 3 generates the image on the analyte holding part 13 based on the image information received from the signal conversion device 2, and displays the generated image on the display portion 3a. The display portion 3a is, for example, a display.

The image processing device 3 calculates the amount of light detected by the photodetector 6 based on the image information received from the signal conversion device 2. The image processing device 3 stores the detection data indicating the relationship between the amount of fluorescent substance and the amount of light detectable by the photodetector 6. The image processing device 3 functions to calculate the amount of fluorescent substance, and calculate the amount of analyte from the calculated amount of fluorescent substance.

The image processing device 3 is a computer configured by CPU, and memory such as ROM and RAM. The various functions of the image processing device 3 are realized when the CPU executes computer programs stored in the memory.

<2> Analyte Detection Method

The analyte detection method used by the analyte detection apparatus 1 of the first embodiment is described below.

FIGS. 5, and 6(a-1) through 6(a-3) are schematic views illustrating the processing sequence of the analyte detection method of the first embodiment.

As shown in FIG. 5(a), a sample S11 containing a dispersed analyte is titrated onto the analyte holding part 13, for example, by a dispenser D1. The sample S11, for example, contains an analyte dispersed in a liquid that contains a hybridization buffer. In this process, a region S21 containing the analyte captured by the capture agent is formed on the analyte holding part 13.

As shown in FIGS. 6(a-1) and 6(a-2), the analyte 31 dispersed in the sample S11 is captured by the capture agent 21 provided on the analyte holding part 13 at this time. For example, when the analyte 31 is a protein and the capture agent 21 is an antibody for the analyte 31, the capture agent 21 captures the analyte 31 protein. The capture agent 21 selectively captures the analyte 31 in the liquid sample and does not capture other substances (contaminants) other than the analyte 31.

As shown in FIG. 5(b), the sample S11 is removed from the analyte holding part 13 using a cleaning liquid W1 such as tris buffer saline with tween 20 or phosphate buffered saline with tween 20. For example, the user may remove only the second unit 1b from the analyte detection apparatus 1 then perform the cleaning.

In this way only the analyte 31 remains in region 21 on the analyte holding part 13. Note that in the above description, the tris buffered saline with tween 20 is also referred to as TBS-T or TBS.

As shown in FIG. 5(c), a fluorescent substance, that is, quantum dots, are preserved beforehand, and a reagent S12 which includes a dispersed bonding substance to bind to the analyte 31 captured by the capture agent 21 is titrated on the region S21 on the analyte holding part 13 via, for example, a dispenser D2. A region S22 is formed on the analyte holding part 13 by this process, and in this region 22 is a complex containing quantum dots, analyte 31, and capture agent 21. As shown in FIG. 6(a-3), a complex containing the binding agent holding the quantum dots, analyte 31, and capture agent 21 is formed in the region S22. The reagent S12, for example, has a dispersion of antibodies holding the quantum dots in a liquid that contains hybridization buffer. The hybridization buffer may be the same as, for example, that contained in the sample S11.

As shown in FIG. 5(d), the reagent S12 is removed from the analyte holding part 13 using a cleaning liquid W2 such as tris buffer saline with tween 20 or phosphate buffered saline with tween 20. For example, the user may remove only the second unit 1b from the analyte detection apparatus 1 then perform the cleaning.

This process removes contaminants from the analyte holding part 13, that is, the process only removes the complex containing the binding agent 41 that holds the quantum dots, analyte 31, and capture agent 21 present in the region S22 on the analyte holding part 13.

Then, as shown in FIG. 5(e), the quantum dots contained in the complex present in region S22 are fluoresced by irradiating light L2 from the light source 11 on the region S22 on the analyte holding part 13. The light K1 given off by the quantum dots is received by the photoelectric conversion element 161 of the photodetector 6.

The photodetector 6 inputs the detection signals corresponding to light K1 to the signal conversion device 2 when the photoelectric conversion element 161 receives the light K1 from the quantum dots. The signal conversion device 2 converts the detection signals received from the photodetector 6 to image information, and outputs the image information to the image processing device 3 via this process. The image processing device 3 generates an image based on the image information and shows the image on the display part 3a.

<3> Quantum Dots

The quantum dots of the first embodiment are described below.

FIG. 6(b-1) is a brief structural view of the quantum dots used in the analyte detection method of the first embodiment, and FIG. 6(b-2) is an energy band diagram of the core 411 and the shell 412 part in FIG. 6(b-1).

As shown in FIG. 6(b-1), the quantum dot 410 is configured by a core 411, a shell 412 covering the core 411, an organic layer 413 covering the shell 412, and a modifying substance 414 bonded to the organic layer 413.

The core 411 is a first semiconductor. As shown in FIG. 6(b-2), the shell 412 is a second semiconductor which has a wider band gap than the first semiconductor. Examples of the combination of the first semiconductor and the second semiconductor include InP/ZnS, CuInS/ZnS, InP/ZnS, CdSe/ZnS and the like.

The quantum dot 410 also may be configured using the same material for both the core 411 and the shell 412. In this case, examples of the first and second semiconductors forming the core 411 and the shell 412 include CdTe, CdSe, CdS and the like.

The organic layer 413 is made of TOPO (trioctylphosphine oxide), HDA (hexadecylamine) and the like.

The modifying layer 414, for example, is made of tripeptide such as glutathione. Note that the modifying layer 414 is not limited to tripeptide, and also may be, for example, a synthetic compound such as polyethyleneimine or thiol, a natural product such as peptide, carbohydrate, phospholipid and the like.

Figure 7:
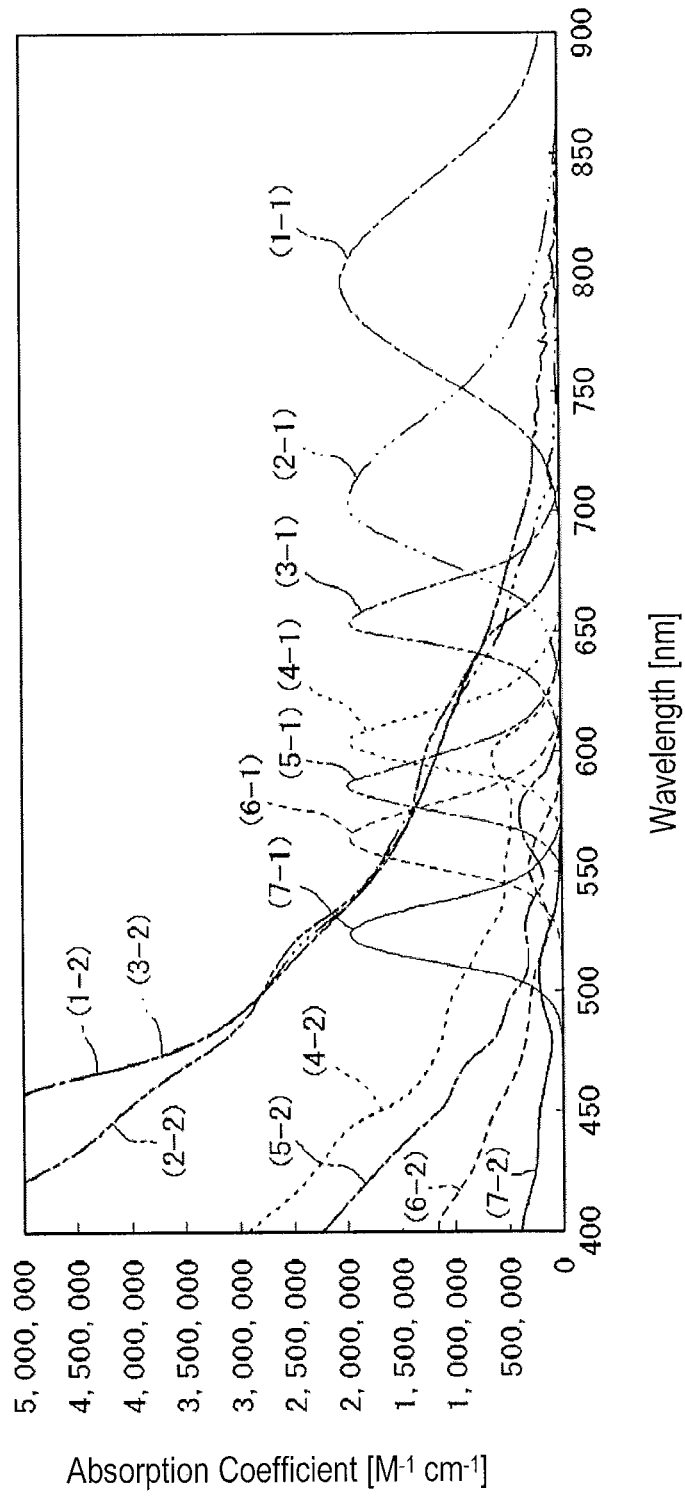
FIG. 7 shows the absorption spectrum and fluorescence spectrum of the quantum dots of the first embodiment.

FIG. 7 shows the absorption spectrum and fluorescence spectrum of the quantum dot 410 of the first embodiment. As shown in FIG. 7, the absorption spectrum and fluorescence spectrum show the measured results of seven types of quantum dots which have a mutually different average particle size. The measured quantum dots 410 have a first semiconductor CdSe forming the core 411, and a second semiconductor ZnS forming the shell 412. Note that in FIG. 7 the absorption spectrum (j–2) (where j=1 through 7) and the fluorescence spectrum (k–1) (where k=1 through 7) correspond to a smaller average particle size the larger the numbers j and k.

As shown in FIG. 7, the fluorescence spectrum (k–1) (where k=1 through 7) is shifted (Stokes shift) to the long wavelength long side relative to the absorption spectrum (j–2) (where j=1 through 7) of the quantum dot 410. The fluorescence spectrum (k–1) (k=1 through 7) of the quantum dot 410 is shifted to the short wavelength long side with decreasing average particle size of the core 411 of the quantum dot 410.

If the quantum dot 410 is used as the fluorescent substance in this way, it is possible to modify the wavelength band of the light emitted from the quantum dot 410 by changing the average particle size of the quantum dot 410. For example, the analyte detection sensitivity can be improved by suitably setting the average particle size of the quantum dot 410 according to the sensitivity characteristics of the photodetector 6. From this perspective, the average particle size of the quantum dot 410 is preferably in the range of 10 to 50 nm.

The quantum dot 410 may be made, for example, using an a chemical synthesis method carried out in the liquid phase. Specifically, particles, in which the surfaces of the core 411 and shell 412 are covered with an organic layer such as TOPO or HDA (hereinafter referred to as "pre-surface modification quantum dot") are made by chemical synthesis in a coordinating organic solvent. Note that the quantum dot also may be made by subjecting the organic layer on the surface of the pre-surface modification quantum dot to a substitution method via an amphiphilic thiol compound (ligand displacement method). Alternatively, the quantum dot is fabricated by covering (encapsulation) the organic layer of the surface pf the pre-surface modification quantum dot with an amphiphilic polymer.

In the above description of the analyte detection method of the first embodiment, the fluorescent substance emits light at a second peak wavelength of 450 nm or higher but not exceeding 900 nm when the fluorescent substance is irradiated by light of a first peak wavelength of 190 nm or higher but not exceeding 350 nm. The light of the second peak wavelength given off by the fluorescent substance is detected by the photodetector 6 with a quantum efficiency of the second peak wavelength which is more than twice the quantum efficiency of the first peak wavelength. Hence, the photodetector 6 can detect the weak light of the second peak wavelength by having the light of the first peak wavelength more difficult to detect than the light of the second peak wavelength to reduce the background level caused by detecting the light of the first peak wavelength. That is, there is an improved S/N ratio of the fluorescent light detection signals. The analyte is therefore detected with high detection sensitivity.

Second Embodiment

The analyte detection method of the second embodiment uses an analyte detection apparatus identical to the analyte detection apparatus of the first embodiment. Although in the first embodiment the analyte 31 is detected by detecting the light of the second peak wavelength given off by the quantum dot using a binding agent which holds the quantum dot as a binding agent to bind to the analyte 31 captured by the capture agent 21, the analyte detection method of the second embodiment differs from the method of the first embodiment in that the analyte 31 is detected by detecting the light of the second peak wavelength given off by the fluorescent substance through a reaction between an enzyme and substrate using an enzyme labeled binding substance as the binding substance for binding to the analyte 31 captured by the capture agent 21. Description of the structure of the analyte detection apparatus is therefore omitted. Only the analyte detection method is described below.

FIGS. 8(*a*) through 8(*d*) and 9(*a*) through 9(*c*) are schematic views illustrating the processing sequence of the analyte detection method of the second embodiment.

A region S21 (refer to FIG. 5(*b*)) is first formed to capture the analyte via the capture agent on the analyte holding part 13 using the same method used in the first embodiment. As shown in FIG. 6(*a*-2), the analyte 31 dispersed in the sample S11 is captured by the capture agent 21 provided on the analyte holding part 13 at this time.

As shown in FIG. 8(*a*), using a dispenser D21, for example, the reagent S212 which contains a dispersion of enzyme labeling binding agent 241 is titrated on the region S21 on the analyte holding part 13. Thus formed on the analyte holding part 13 is a region S23 which includes a complex containing the capture agent 21, analyte 31, and enzyme labeling binding agent 241. The reagent S212, for example, is a dispersion of enzyme labeled antibodies in a liquid containing a hybridization buffer. For example, peroxidase or alkaline phosphatase may be used as the enzyme (2411 in FIGS. 9(*a*) and 9(*b*)). The hybridization buffer, for example, may be the same buffer contained in the sample S11 described in the first embodiment.

Figure 9A:
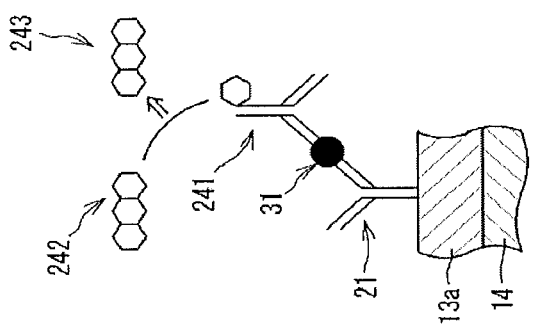
FIGS. 9(a) through 9(c) schematically illustrate the processing sequence of the analyte detection method of a second embodiment.
Figure 9B:
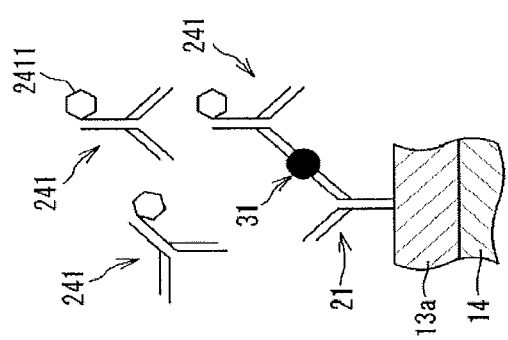

As shown in FIGS. 9(*a*) and (*b*), the enzyme labeling binding agent 241 which is dispersed in the reagent S212 binds to the analyte 31 captured by the capture agent 21 in the region S23. Hence, a complex is formed which contains the capture agent 21, analyte 31, and enzyme labeled binding agent 241.

As shown in FIG. 8(*b*), the reagent S212 is removed from the analyte holding part 13 using a cleaning liquid W22 such as tris buffer saline with tween 20 or phosphate buffered saline with tween 20. In this way only the complex remains in region S23 on the analyte holding part 13. The second unit 1*b* may be removed from the analyte detection apparatus 1 for cleaning of the second unit 1*b* at this time.

As shown in FIG. 8(*c*), using a dispenser D22, for example, the reagent S213 which contains a dispersion of fluorescent substance is titrated on the region S23 of the analyte holding part 13. The reagent S213, for example, contains a fluorescent substance dispersed in a liquid that contains a hybridization buffer.

Examples of useful fluorescent substances include peroxidase fluorescent substrate to produce a resorufin fluorescent substance by reacting with peroxidase, or alkaline phosphatase fluorescent substrate to produce a BBT-anion fluorescent substance by reacting with alkaline phosphatase. Note that resorufin produced from peroxidase fluorescent substrate is a fluorescent substance that gives off strong fluorescence compared to, for example, organic dyes. BBT-anion produced from alkaline phosphatase fluorescent substrate is a fluorescent substance that has a large Stokes shift and broad fluorescence spectrum compared to, for example, organic dyes. The hybridization buffer may be the same as, for example, that contained in the reagent S212.

This process disperses the fluorescent substrate 242 and fluorescent substance 243, which was produced by reacting with the enzyme of the complex present in region S23, in the reagent S213. Formed on the analyte holding part 13 at this time is a region S24 containing the fluorescent substance 243 produced by the reaction between the fluorescent substrate 242 and the enzyme.

Figure 9C:
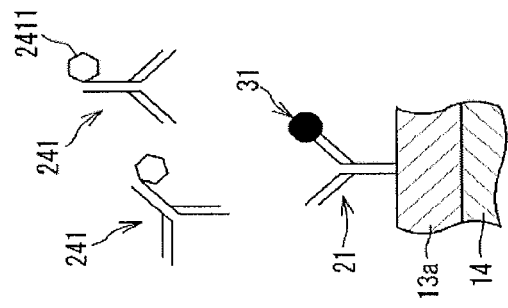

As shown in FIG. 9(c), the fluorescent substrate 242 reacts with the enzyme of the complex present in region S23 to produce the fluorescent substance 243. For example, when the enzyme is peroxidase, the enzyme reacts with the peroxidase fluorescent substrate to produce resorufin, that is, the fluorescent substance 243.

Figure 8A:
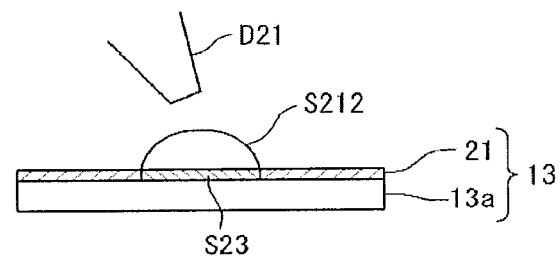
FIGS. 8(a) through 8(d) schematically illustrate the processing sequence of the analyte detection method of a second embodiment.
Figure 8B:
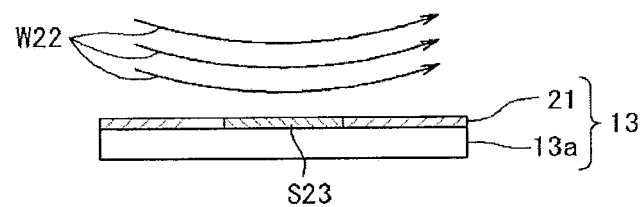
Figure 8C:
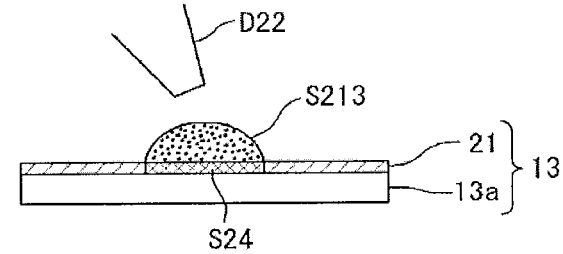
Figure 8D:
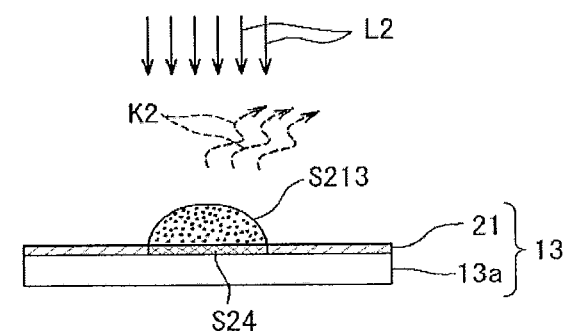

Thereafter, the fluorescent substance 243 dispersed in the reagent S213 is fluoresced/by irradiating light L2 from the light source 11 on the region S24 containing the fluorescent substance 243 produced by the reaction between the enzyme and the fluorescent substrate 242, as shown in FIG. 8(d). The light K2 given off by the fluorescent substance 243 is received by the photoelectric conversion element 161 of the photoreceptor 16.

In the above description of the analyte detection method of the second embodiment, the fluorescent substance emits light at a second peak wavelength of 450 nm or higher but not exceeding 900 nm when the fluorescent substance is irradiated by light of a first peak wavelength of 190 nm or higher but not exceeding 350 nm. The light of the second peak wavelength given off by the fluorescent substance is detected by the photodetector 6 with a quantum efficiency of the second peak wavelength which is more than twice the quantum efficiency of the first peak wavelength. Hence, the photodetector 6 can detect the weak light of the second peak wavelength by having the light of the first peak wavelength more difficult to detect than the light of the second peak wavelength to reduce the background level caused by detecting the light of the first peak wavelength. That is, there is an improved S/N ratio of the fluorescent light detection signals. The analyte is therefore detected with high detection sensitivity.

In the analyte detection method of the first and second embodiments, the photodetector 6 is arranged in the fluorescent substance, photodetector 6 order in the direction of the irradiation of the light of the first peak wavelength when the light of the first peak wavelength is emitted. Even in a configuration in which both the light of the first peak wavelength emitted from the light source 11 and the light of the second peak wavelength given off by the fluorescent substance of the complex present on the analyte holding part 13 readily enter the photodetector 6, the light of the first peak wavelength is more difficult to detect than the light of the second peak wavelength because the photodetector 6 has a quantum efficiency at the second peak wavelength that is more than twice the quantum efficiency at the first peak wavelength. Therefore, the weak light of the second peal wavelength can be detected because the back ground level is reduced through detecting the light of the first peak wavelength.

Note that the monochrome CMOS image sensor of the photodetector 106 of the first and second embodiments increases the quantum efficiency compared to a color CMOS image sensor using the same photoelectric conversion element because some of the incident light is not absorbed by the color filter.

Third Embodiment

Figure 10:
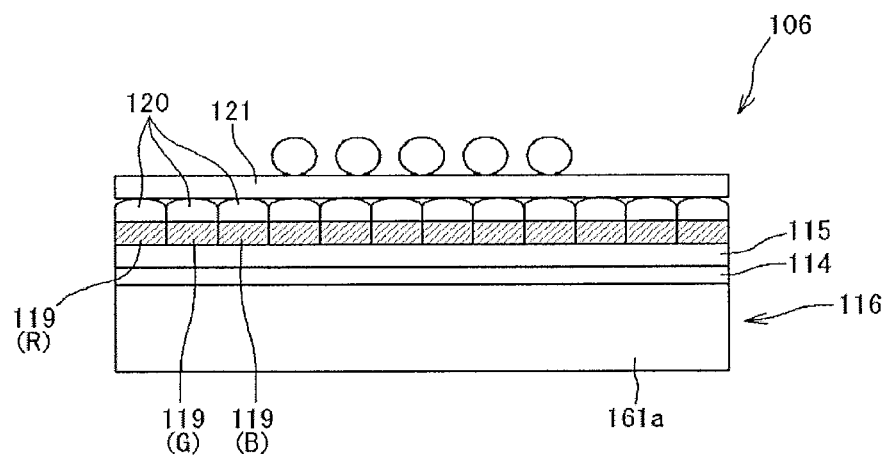
FIG. 10 is a brief structural view of the photodetector of the analyte detection apparatus of a third embodiment viewed from the side.

The third embodiment differs from the first embodiment in the structure of the photodetector 106, as shown in FIG. 10. The analyte detection method and the structure of the analyte detection apparatus excluding the photodetector 106 are identical method and structure of the first and second embodiments.

The photodetector 106 of the third embodiment is a color CMOS image sensor configured by a photoreceptor 116, color filter 119, micro lens 120, cover member 121. The photoreceptor 116 is configured by a photoelectric conversion element 161a, a first protective layer 114 and second protective layer 115 both provided on the photoelectric conversion element 161a. The photoelectric conversion element 161a, first protective layer 114 and second protective layer 115 are laminated from below in this order. The photoelectric conversion element 161a may use a photodiode identical to the first embodiment. The first protective layer 114 is a silicon nitride film identical to that of the first embodiment. The second protective layer 115 is a silicon oxide film identical to that of the first embodiment.

The color filter 119 is provided in plurality on the photoreceptor 116. The plurality of color filters 119 are absorption filters which respectively selectively transmit light of specific wavelength and absorb the light of other wavelengths. Specifically, the plurality of color filters 119 transmit light of the red, green, and blue wavelengths, respectively. Therefore, the photodetector 106 recognizes and detects light of at wavelengths of a plurality of colors, that is, visible light of several colors, via the color filters 119.

The photodetector 106 functions, via the color filters 119, as a first sensor which has spectral sensitivity of red color at a peak wavelength in the range of 620 nm or higher but not exceeding 750 nm, a second sensor which has spectral sensitivity of green color at a peak wavelength in the range of 495 nm or higher but not exceeding 570 nm, and a third sensor which has spectral sensitivity of blue color at a peak wavelength in the range of 450 nm or higher but not exceeding 495 nm.

The red filter R of the color filter 119 of the first sensor is a first absorption unit for absorbing light outside the red wavelength range. The green filter G of the color filter 119 of the second sensor is a second absorption unit for absorbing light outside the green wavelength range. The blue filter B of the color filter 119 of the third sensor is a third absorption unit for absorbing light outside the blue wavelength range.

The micro lens 120 is provided in plurality to correspond to each color filter 119. Each micro lens 120 gathers light impinging from above on the photoelectric conversion element 161a of the photoreceptor 116 through the color filter 119.

The cover member 121 is a transparent panel such as a glass plate, and covers the micro lens 120 from above. The complex which contains the analyte is provided on the cover member 121, and is irradiated from above by the excitation light emitted from the light source 11. The cover member 121 functions as the base 13a of the first and second embodiments when using a complex containing an analyte as described in the first and second embodiments.

Figure 11:
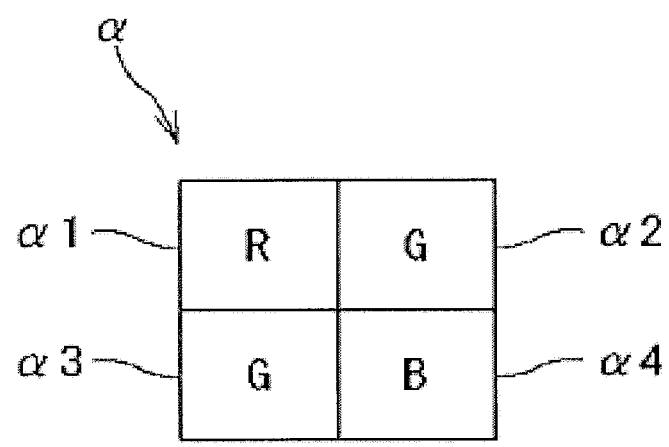
FIG. 11 shows the pattern of the color filter allocated to one pixel of the photodetector in the third embodiment.

The plurality of color filters 119 are aligned in the pattern shown in FIG. 11. Specifically, one pixel α of the CMOS image sensor of the photodetector 106 is divided into 4 blocks α1 through α4 in a 2×2 array, wherein the red filter R is provided for one pixel α1, the blue filter B is provided for another pixel α4, and the green filter G is provided for the remaining two pixels α2 and α3. The pattern shown in FIG. 11 is arranged regularly throughout the entire photoreceptor 116.

Figure 12:
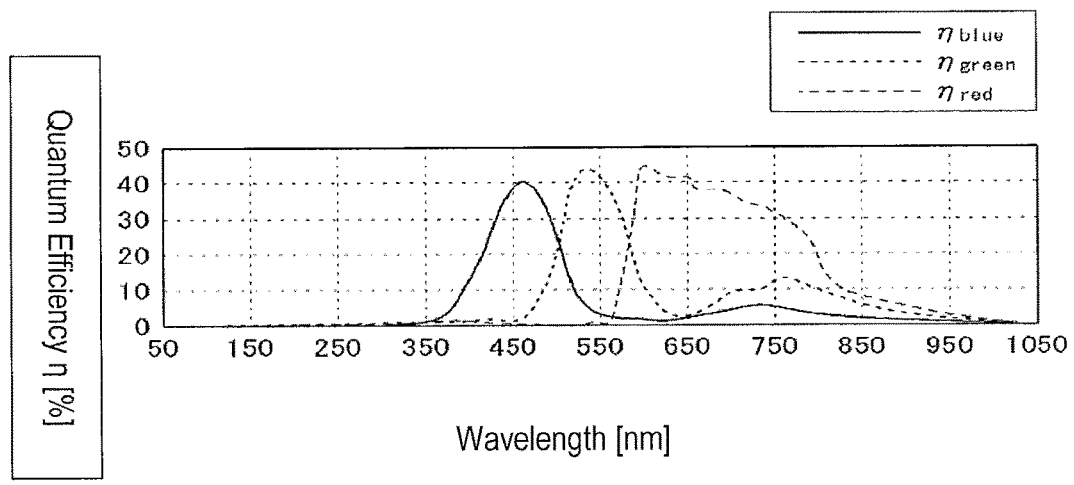
FIG. 12 shows the sensitivity characteristics of different colors of the photodetector in the third embodiment.

FIG. 12 shows the quantum efficiency of the color filter for each color per block of one pixel of the color CMOS image sensor. ηred, ηgreen, and ηblue are respectively the quantum efficiencies of each block α1 through α4 provided with the red filter R, green filter G, and blue filter B.

On the other hand, the quantum efficiency ηpixel per pixel α of the color CMOS image sensor shown in FIG. 11 represents the average quantum efficiency of all blocks α1 through α4 of the pixel α. That is, the quantum efficiency ηpixel can be determined by equation (1) shown below.

$$\eta pixel = (\eta blue + \eta green + \eta green + +\eta red)/4 \qquad (1)$$

$$= 1/4\eta blue + 1/2\eta green + 1/4\eta red$$

Figure 13:
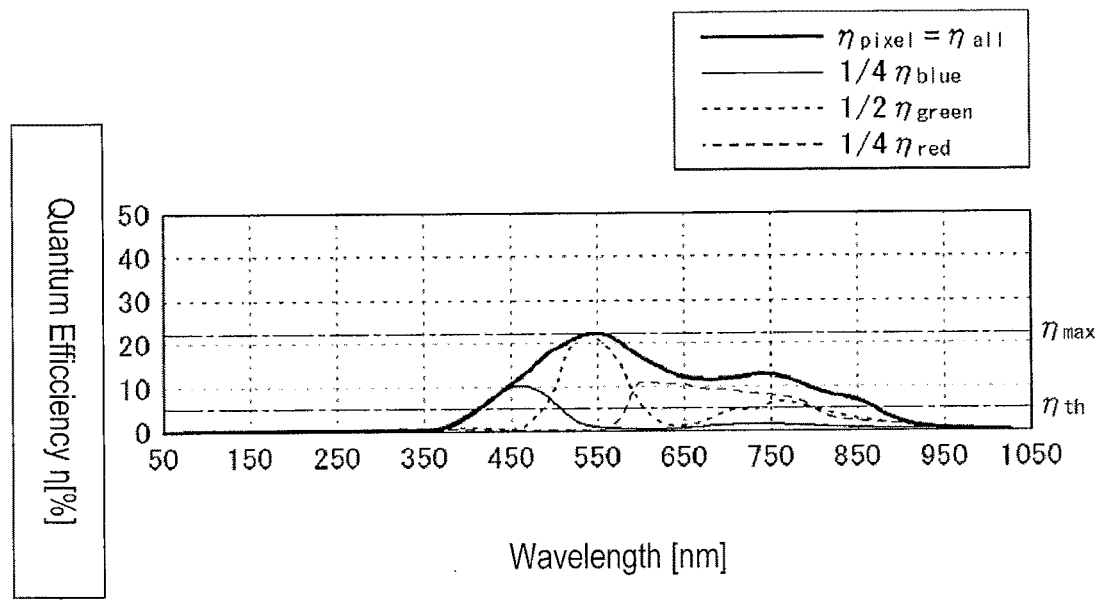
FIG. 13 shows the sensitivity characteristics per pixel of the photodetector in the third embodiment.

FIG. 13 shows the quantum efficiency of ηpixel, and the components ¼ ηblue, ½ ηgreen, and ¼ ηred, per one pixel α. Since the color CMOS image sensor is configured by integrating a plurality of pixels α, the quantum efficiency pixel per one pixel α and the quantum efficiency ηall of the entire color CMOS image sensor are identical. That is, equation (2) below is satisfied.

$$\eta all = \eta pixel \qquad (2)$$

In FIG. 13, ηmax represents the maximum value of the quantum efficiency pixel per one pixel α, that is, quantum efficiency ηall of the color CMOS image sensor represents the maximum value, and ηth represents the quantum efficiency 5%. The wavelength at quantum efficiency ηmax is in the range of 450 nm or higher but not exceeding 900 nm. The photodetector 106 of the embodiment configuring the color CMOS image sensor has a quantum efficiency of approximately 0% relative to the light at the first peak wavelength of 190 nm or higher but not exceeding 350 nm emitted from the light source 11. The quantum efficiency of the light of the second peak wavelength given off by the fluorescent substance, however, is approximately 22% as shown in FIG. 13. Therefore, even when using the photodetector 106 of the third embodiment, the quantum efficiency at the second peak wavelength is more than twice the quantum efficiency at the first peak wavelength.

Hence, the photodetector 6 can detect the weak light of the second peak wavelength by having the light of the first peak wavelength more difficult to detect than the light of the second peak wavelength to reduce the background level caused by detecting the light of the first peak wavelength. That is, there is an improved S/N ratio of the fluorescent light detection signals. The analyte is therefore detected with high detection sensitivity. The photodetector 106 can recognize and detect the color of the light at the second peak wavelength.

Modifications

Note that the present invention is not limited to the embodiments described above, and includes all modes set forth within the range of the appended claims. For example, the following modifications are included.

Although the analyte detection method of the first through third embodiments are described by way of examples using the present invention to detect an analyte, the present invention is not limited to these examples. For example, the present invention is not limited to analyte and also may be used in fluorescence detection methods for detecting the fluorescence from a fluorescent substance. In this case, the capture agent used in the first through third embodiments is not essential. Therefore, the device used in the fluorescence detection method may be a device used in place of the substrate 13a and the analyte holding part 13 of the analyte detection apparatus 1 of the first embodiment.

Although the first through third embodiments are described by way of examples in which the first peak wavelength is 270 nm, the present invention is not limited to this wavelength. In the present invention, the first peak wavelength may be 190 nm or higher but not exceeding 250 nm.

Figure 14:
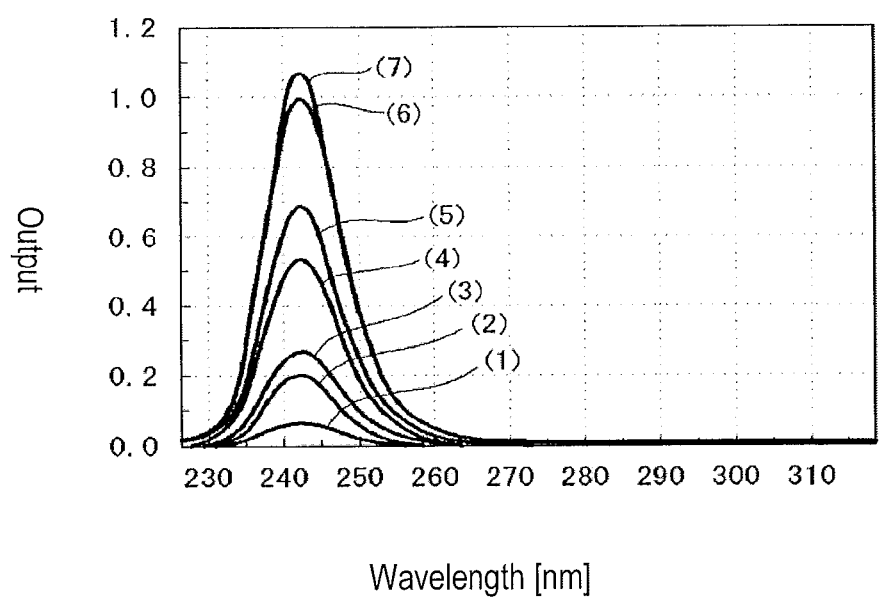
FIG. 14 shows an example of the optical spectrum of deep ultraviolet light emitted from the LED in a modification.

In the present invention, the first peak wavelength also may be, for example, between 242 to 243 nm as shown in FIG. 14. FIG. 14 shows an example of the optical spectrum of deep ultraviolet light emitted from the LED in a modification. Note that FIG. 14 shows the optical spectrum when the size of the bias in the sequence direction toward the LED is set to each of the sizes of the seven types of particles. In FIG. 14, the sequence direction bias increases as the numbers (1) through (7) increase.

Note that the first peak wavelength is preferably 240 nm or higher in the present invention from the perspective of higher strength of the fluorescent light detection signal since the output of the light from the light source decreases as the wavelength becomes shorter. The first peak wavelength is preferably 300 nm or lower in the present invention from the perspective of suppressing the background level of the detection signals caused by the light impinging the photodetector. The first peak wavelength thus is preferably 300 nm or lower in the present invention from the perspective of improving the S/N ratio of the fluorescence output signal. Note that general purpose light sources outputting a wavelength higher than 190 nm are readily available. When the wavelength of the light emitted from the light source is greater than 350 nm, however, there is a possibility that light from a light source will be detected by a general purpose photodetector and cause background noise.

Although the first through third embodiments are described by way of examples in which the second peak wavelength is 705 nm, the present invention is not limited to this wavelength. In the present invention, the second peak wavelength may be 450 nm or higher but not exceeding 900 nm. In the present invention, a general purpose photodetector and fluorescent substance are readily usable and ideally suited insofar as the second peak wavelength is 830 nm or lower, since the Illuminating Engineering Institute of Japan has defined brightness using spectral sensitivity from 360 nm to 830 nm. Therefore, the second peak wavelength is preferably 450 nm or higher but not exceeding 830 nm.

Although the analyte detection methods of the first through third embodiments are described by way of examples in which the photodetectors 6 and 106 have 0% quantum efficiency at the first peak wavelength and approximately 40% or 22% quantum efficiency at the second peak wavelength, the present invention is not limited to these quantum efficiencies. In the present invention, the photodetectors may have a quantum efficiency at the second peak wavelength which is double or greater than the quantum efficiency at the first peak wavelength.

Note that in the present invention the photodetector preferably has a quantum efficiency less than 10% relative to the first peak wavelength from the perspective of suppressing the background level of the detection signals which is caused by light impinging the photodetector. In other words, the first peak wavelength is preferably a wavelength which cannot be detected at a quantum efficiency above 10% by the photodetector. This configuration improves the S/N ratio of the fluorescent light detection signals.

In the present invention the photodetector more preferably has a quantum efficiency less than 5% relative to the first peak wavelength from the perspective of suppressing the background level of the detection signals which is caused by light impinging the photodetector. In other words, the first peak wavelength is more preferably a wavelength which cannot be detected at a quantum efficiency above 5% by the photodetector. This configuration improves the S/N ratio of the fluorescent light detection signals.

Although the analyte detection methods of the first through third embodiments are described by way of examples in which the photodetectors 6 and 106 use a CMOS image sensor incorporating a photoelectric conversion element which uses a silicon substrate, the present invention is not limited to this configuration.

Note that the quantum efficiency is reduced relative to the first peak wavelength in the photodetectors since the photodetectors incorporate a photoelectric conversion element using a silicon substrate and silicon blocks the light of the first peak wavelength of 190 nm and greater but less than 350 nm. Therefore, it is preferable that the photodetector incorporates a photoelectric conversion element which uses a silicon substrate from the perspective of suppressing the background level of the detection signals caused by light impinging the photodetector. Specifically, CMOS image sensor, micro PMT (photomultiplier tube), piN (positive-intrinsic-Negative) photodiode, APD (avalanche photodiode), MPCC (multi pixel photon counter), EMCCD (electron multiplying charge coupled device), CCD (charge coupled device) image sensor, or NMOS (negative channel metal oxide semiconductor) image sensor may be used as the photodetector incorporating a photoelectric conversion element using a silicon substrate. Among these, the CMOS image sensor and micro PMT are preferable for the photodetector in the present invention because the CMOS image sensor and micro PMT improve the S/N ratio of the fluorescent light detection signals due to the particularly low quantum efficiency at the first peak wavelength.

Although the analyte detection method of the first through third embodiments has been described by way of examples using quantum dots as a fluorescent substance, the present invention is not limited to this configuration. For example, organic dyes also may be used as the fluorescent substance. Examples of useful organic dyes include organic dyes synthesized from coumarin, rohdamine, xanthene, or cyanine.

Figure 15:
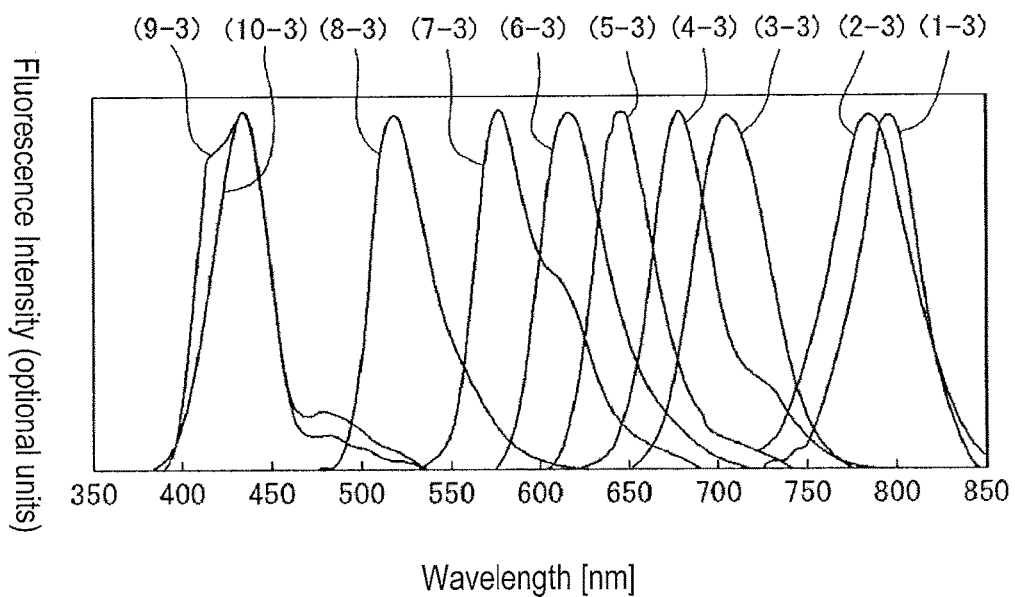
FIG. 15 shows the fluorescence spectrum of the organic dye of the modification.

FIG. 15 shows an example of the fluorescence spectrum of an organic dye used in a modification of the analyte detection method. The organic dyes shown in the examples are invariably manufactured by Molecular Probes, Inc. In FIG. 15 (1-3) corresponds to Alexa Fluor 790, (2-3) corresponds to Alexa Fluor 750, (3-3) corresponds to Alexa Fluor 680, (4-3) corresponds to Alexa Fluor 647, (5-3) corresponds to Alexa Fluor 633, (6-3) corresponds to Alexa Fluor 594, (7-3) corresponds to Alexa Fluor 555, (8-3) corresponds to Alexa Fluor 488, (9-3) corresponds to Alexa Fluor 405, and (10-3) corresponds to Alexa Fluor 355.

Note that other organic dyes, such as Alexa Fluor 430, Alexa Fluor 532, Alexa Fluor 546, Alexa Fluor 568, Alexa Fluor 660, Alexa Fluor 680, and Alexa Fluor 700 invariably manufactured by Molecular Probes, Inc.) also may be used.

Examples of other organic dyes include 9-phenylxanthene based dyes, cyanine dyes, metallo cyanine dyes, xanthene dyes, triphenylmethane dyes, acridine dyes, oxazine dyes, coumarin dyes, merocyanine dyes, rhodacyanine dyes, polymethine dyes, porphyrin dyes, phthalocyanine dyes, rhodamine dyes, xanthene dyes, chlorophyll-based dye, eosin dyes, mercurochrome based dyes, indigo based dyes, BODIPY based dyes, CALFluor dyes, Oregon Green dyes, rhodol green, Texas red, Cascade blue, nucleic acid (DNA, RNA and the like), cadmium selenide, cadmium telluride, $Ln_2O_3$:Re, $Ln_2O_2S$:Re, ZnO, $CaWO_4$, Mo-x$Al_2O_3$:Eu, $Zn_2SiO_4$:Mn, $LaPO_4$:Ce, Tb, Cy3, Cy3.5, Cy5, Cy5.5, Cy7, Cy7.5, and Cr9 (invariably manufactured by Amersham Biosciences, Inc.); DY-610, DY-615, DY-630, DY-631, Dy-633, DY-635, DY-636, EVO blue 10, EVO blue 30, DY-647, DY-650, DY-651, DY-800, DYQ-660, and DYQ-661 (invariably manufactured by Dyomics, Inc.); Atto 425, Atto 465, Atto 488, Atto 495, Atto 520, Atto 532, Atto 550, Atto 565, Atto 590, Atto 594, Atto 610, Atto611x, Atto 620, Atto 633, Atto 635, Atto 637, Atto 647, Atto 655, Atto 680, Atto 700, Atto 725, and Atto 700 (invariably manufactured by Atto-TEC GmbH Co.; VivoTag 5680, VivoTag 680, and VivoTag S750 (invariably manufactured by VisEn Medical, Inc.). Note that Ln above represents La, Gd, Lu, or Y; Re represents lanthanide elements, M represents alkaline earth metals, and x represents a number from 0.5 to 1.5.

Note that the quantum dots are unlikely to fade due to the light emitted from a light source due to their higher brightness compared to, for example, organic dyes and fluorescent proteins. Accordingly, since fluorescent substances such as organic dyes and fluorescent proteins are more likely to fade due to short wavelength light than by long wavelength light, using quantum dots as the fluorescent substance is unlikely to result in fading by short wavelength light and is also advantageous for detection of a small amount of analyte as well as viewing analyte over a long period even when the fluorescent substance is irradiated by short wavelength light. In the present invention, therefore, the quantum dot is preferable as the fluorescent substance.

Although the first through third embodiments are described by way of examples in which the light source 11 is configured by a semiconductor light emitting element such as an LED, the type of light source 11 is not limited to this example. For example, the light source 11 also may be configured by a discharge lamp (for example, HID lamp).

Although the first through third embodiments are described by way of examples in which one type of peptide such as glutathione is used as the modifying substance 414 of the electron dot 410, the modifying substance 414 is not limited to only one type of organic substance. For example, the modifying substance 414 also may be configured by a peptide, and ligand to a receptor or antibody bound to the peptide.

Although the photodetector 106 of the third embodiment is provided with an absorption filter as a filter for transmitting some of the light given off by the fluorescent substance, an interference filter also may be used in place of the absorption filter. Although the photodetector 106 of the third embodiment is provided with three color filters of red, green and blue as the color filter 119, three color filter of cyan, magenta, and yellow also may be provided. The photodetector 106 also may not be provided with a color filter. For example, a laminate type image sensor for recognizing and detecting a plurality of colors using a different depth of absorption for each color, organic film image sensor stacked on a photoelectric conversion layer, or an optical image sensor provided with an optical unit such as a deflector may be used as the photodetector 106.

EXAMPLES

Although the present invention is described in detail by way of the following examples, the present invention is not limited to these examples.

Example 1

Fluorescent Substance Immobilization on CMOS Image Sensor

A cover glass, which was prepositioned on a monochrome CMOS image sensor of the photodetector 6 of the first embodiment, is first removed, and TBS-T as a reference sample and a sample containing 1 µM of quantum dots as a fluorescent substance are titrated on a micro lens array which is arranged in a two-dimensional array. Then, the samples are dried by allowing the CMOS image sensor to stand in a 50° C. environment for 10 minutes. Note that the sensitivity characteristics of the CMOS image sensor are shown in FIG. 3. Also Note that an MT9M001 manufactured by Aptina Imaging, Inc. is used as the monochrome CMOS image sensor. Qdot 705 streptavidin conjugate Q10163MP manufactured by Life Technologies, Inc. was used as quantum dots.

(Excitation Light)

Excitation light was then irradiated from overhead and through a diffuser onto the top of the CMOS image sensor. The excitation intensities were maximized in a range that did not saturate the pixel values of the CMOS image sensor. In comparative example 1, light of a peak wavelength of 470 nm was irradiated using a blue LED light source. In comparative example 2, light of a peak wavelength of 365 nm was irradiated using an ultraviolet LED light source.

In the main example, light of a peak wavelength of 270 nm was irradiated using a deep ultraviolet LED light source.

(Experimental Results)

FIG. 16(a-1) is an image obtained by a comparative example 1, FIG. 16(b-1) is an image obtained by a comparative example 2, and FIG. 16(c-1) is an image obtained by example 1. FIG. 16(a-2) shows intensity profile at the A-A line of FIG. 16(a-1), FIG. 16(b-2) shows the intensity profile at the A-A line of FIG. 16(b-1), and FIG. 16(c-2) shows the intensity profile at the A-A line of FIG. 16(c-1). In the graphs of FIGS. 16(a-2), 16(b-2), 16(c-2), the position on the A-A line represents the X coordinate.

As shown in the case of comparative example 1 of FIGS. 16(a-1) and 16(a-2), the detection intensity of the region with added quantum dots (hereinafter referred to as "region S25) and the detection intensity of the region with TBS-T added as reference (hereinafter referred to as "region Ref") in the image are low compared to the detection intensity of other regions in the image. This is thought to result from the higher background level of the detection signals output from the CMOS image sensor due to the presence of the peak wavelength (470 nm) light emitted from the blue LED light source within the relatively high wavelength band.

As shown in the case of comparative example 2 of FIGS. 16(b-1) and 16(b-2), the detection intensity in region S25 is high compared to the detection intensity in regions in the image excluding region S25 and region Ref. The detection intensity in region Ref is rather low compared to the detection intensity in regions in the image excluding region S25 and region Ref. The CMOS image sensor is thought to reduce the background level of the detection signals output from the CMOS image sensor compared to comparative example 1 because the sensitivity to the light of the peak wavelength of 365 nm in comparative example 2 is lower than that of the light of the peak wavelength of 470 nm in comparative example 1. In the case of comparative example 2, the background level of the detection signals is approximately 80% of the detection intensity in region S25, and the S/N ratio of the detection signals cannot be said to be sufficiently high.

As shown in the case of example 1 of FIGS. 16(c-1) and 16(c-2), the detection intensity in region S25 is extremely high compared to the detection intensity in regions in the image excluding region S25 and region Ref. The detection sensitivity in region Ref is approximately the same as the background level, and extremely low compared to the detection sensitivity in region S25. The CMOS image sensor is thought to suppress an increase in the background level because the sensitivity at the 270 nm wavelength is approximately zero. In the case of example 1, the background level of the detection signal is about 4% of the detection intensity in region S25, a sufficiently high S/N ratio.

It can be understood from these results that an increase in the background level of the detection signal output from the CMOS image sensor can be suppressed and the S/N ratio of the fluorescent light detection signal can be improved by setting the peak wavelength of the light that irradiates the fluorescent substance at the 270 nm wavelength which does not influence the sensitivity of the CMOS image sensor, and setting the wavelength of the fluorescent light given off by the fluorescent substance at the 705 nm wavelength for which the CMOS image sensor is sufficiently sensitive.

Example 2

1 µM of quantum dots shown below as a fluorescent substance and 0.5 µL of each of the references were titrated on the cover member 121 of the color CMOS image sensor of the photodetector 106 shown in FIG. 10, and dried by heating for 10 minutes at 50° C. A fluorescent image was obtained by irradiating deep ultraviolet light at 270 nm wavelength from the LED light source as example 2. A bright-field image was obtained by irradiating ultraviolet light at 405 nm wavelength from a light source as a comparative example.

An MT9M001C12STC manufactured by Aptina Imaging, Inc. was used as the color CMOS image sensor.

Reference (1) below was used, and quantum dots (2) through (6) were used.

(1) TBS
(2) Qdot 525 streptavidin conjugate Ex. 425 nm/Em. 525 nm (Q10141MP, Life Technologies, Inc).
(3) Qdot 585 streptavidin conjugate Ex. 425 nm/Em. 585 nm (Q10111MP, Life Technologies, Inc).
(4) Qdot 625 streptavidin conjugate Ex. 425 nm/Em. 625 nm (A10196, Life Technologies, Inc).
(5) Qdot 705 streptavidin conjugate Ex. 425 nm/Em. 705 nm (Q10161, Life Technologies, Inc).
(6) Qdot 800 streptavidin conjugate Ex. 425 nm/Em. 800 nm (Q10173MP, Life Technologies, Inc).

Figure 17A:
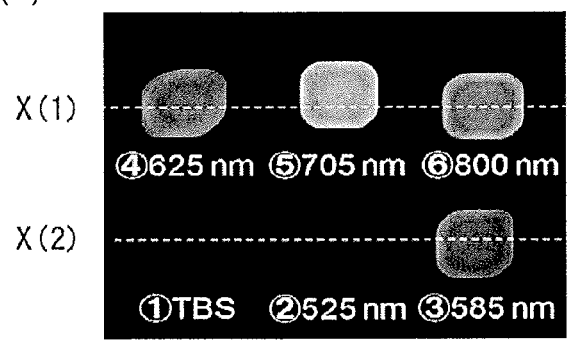
FIG. 17(a) shows an image obtained by example 2.
Figure 17B:
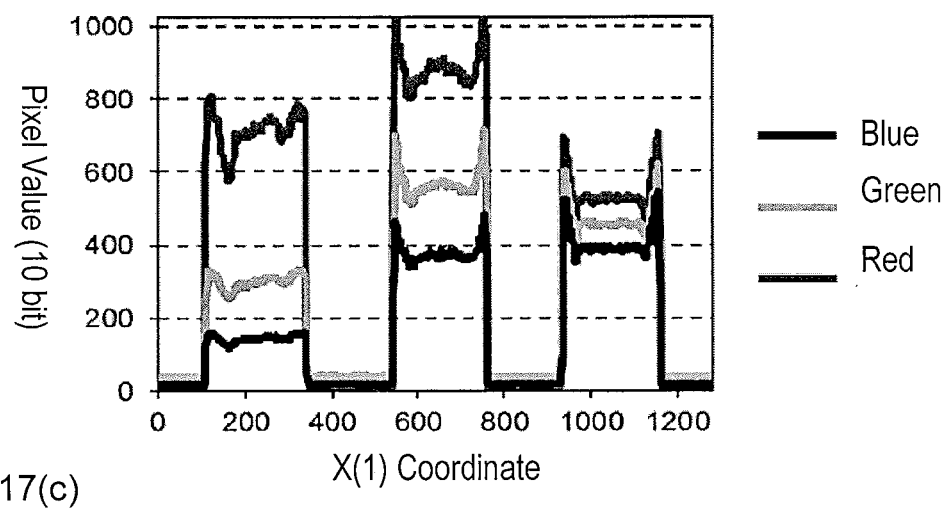
FIG. 17(b) shows the intensity profile on the X(1) axis of the image of FIG. 17(a)
Figure 17C:
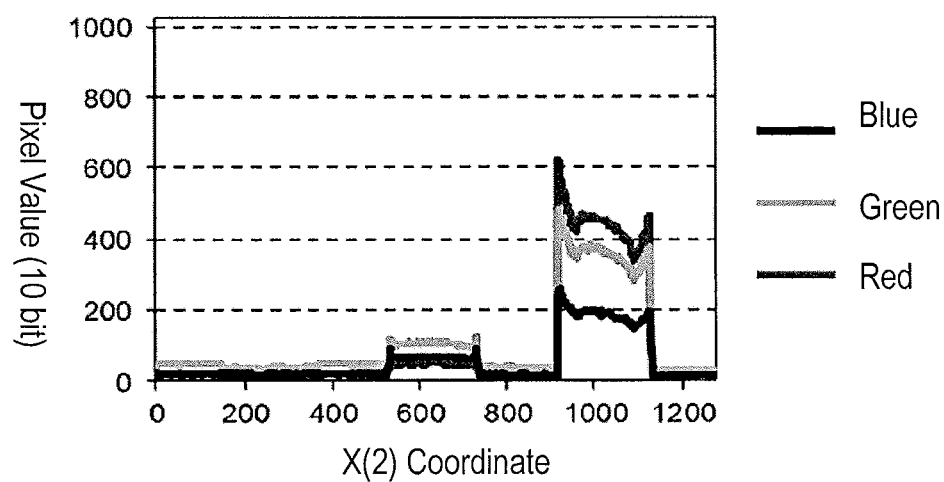
FIG. 17(c) shows the intensity profile on the axis of X(2) of same.
Figure 18A:
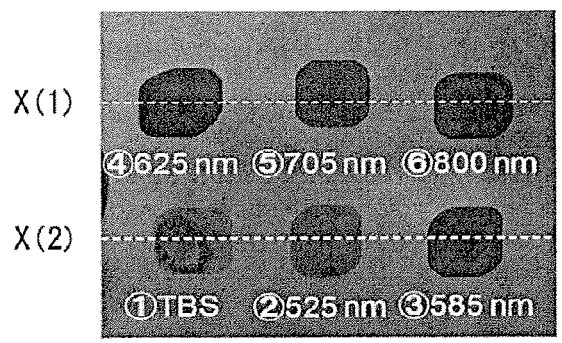
FIG. 18(a) shows an image obtained by a comparative example.
Figure 18B:
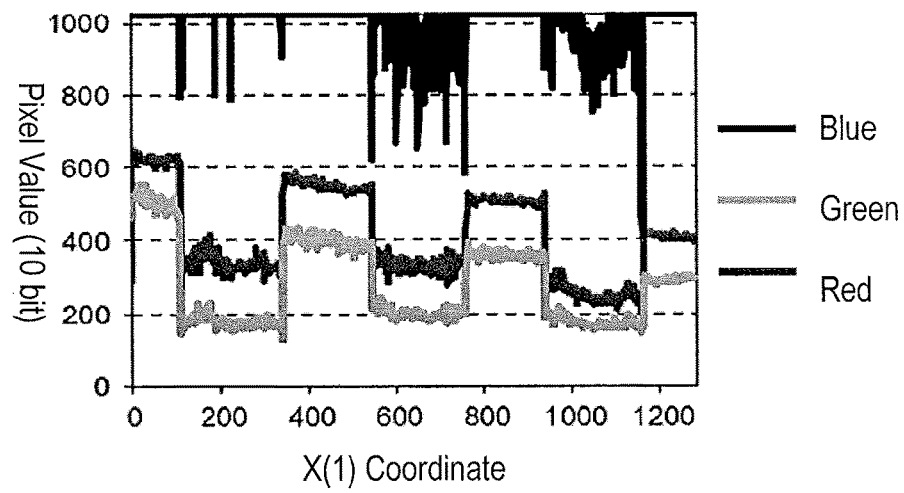
FIG. 18(b) shows the intensity profile on the X(1) axis of the image of FIG. 18(a)
Figure 18C:
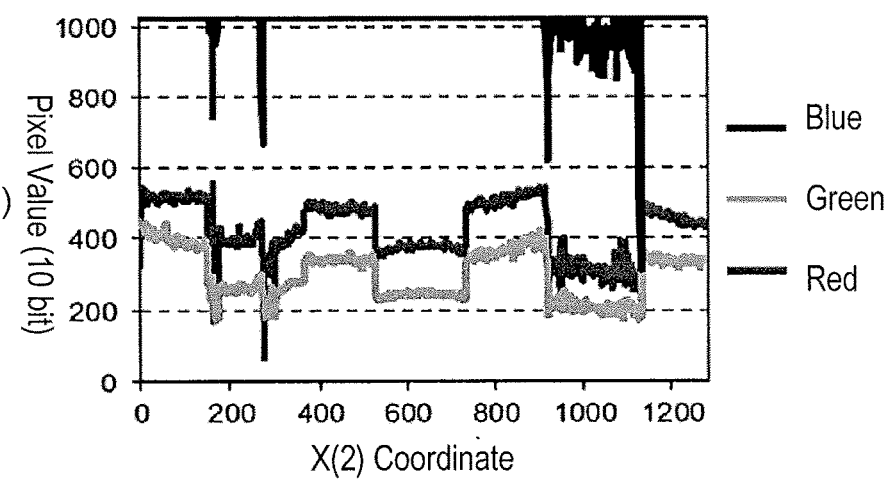
FIG. 18(c) shows the intensity profile on the axis of X(2) of same.

The results of example 2 are shown in FIGS. 17(a) through 17(c) and the results of the comparative example are shown in FIGS. 18(a) through 18(c). FIG. 17(a) and FIG. 18(a) show a fluorescent image and bright-field image, respectively. The circled numbers 1 through 6 and wavelength values on the respective images correspond to reference of (1) and quantum dots of (2) through (6) above. FIG. 17(b) and FIG. 18(b) show the intensity profile on the X(1) axis indicated by the dotted line in the images of FIG. 17(a) and FIG. 18(a). FIG. 17(c) and FIG. 18(c) show the intensity profile on the X(2) axis indicated by the dotted line in the images of FIG. 17(a) and FIG. 18(a).

In the comparative example shown in FIGS. 18(a) through 18(c), in the reference of (1) above and all quantum dots (2) through (6) above the blue detection intensity increased, and the blue detection sensitivity increased in the surroundings. It is thought that the background level of the detection signals output from the photodetector 106 increased because the ultraviolet light peak wavelength 405 nm overlaps the spectral sensitivity of the photodetector 106 to the color blue. On the other hand, the red, green, and blue detection intensity in the regions of the reference and the quantum dots is lower than detection intensity in the surrounding areas. Hence, the bright-field image of the reference and quantum dots is confirmed.

In example 2 shown in FIGS. 17(a) through 17(c), the fluorescent light given off by the quantum dots (2) through (6) is detected by color according to the wavelength, and the detection intensity surrounding the quantum dots is extremely low. Reference (1) did not give off fluorescent light and was virtually undetectable. Thus, the fluorescent light detection signal S/N ratio improved and the fluorescent substance was detectable with high detection sensitivity. When using the photodetector 106 of the third embodiment, the bright-field image and plurality of color fluorescent images were both obtained by changing the wavelength of the light source.

Example 3

10 μL fluorescent beads were used as the fluorescent substance shown in (2) through (5) below and 10 μL of non-fluorescent beads shown in (1) below were poured in a 50 μL solution and titrated on the cover member 121 of a color CMOS image sensor of the photodetector 106 shown in FIG. 10, then dried by heating at 50° C. for 30 minutes. A fluorescent image was obtained by irradiating deep ultraviolet light at 270 nm peak wavelength from the LED light source as example 3. A bright-field image was obtained by irradiating ultraviolet light at 405 nm wavelength from a light source as a comparative example.

The non-fluorescent beads of (1) below were used, and fluorescent beads of (2) through (5) below were used.

(1) 15 μm polystyrene non-fluorescent beads (18328, Poly Science Co., Ltd.).
(2) 15 μm polystyrene fluorescent beads Ex. 365 nm/Em. 415 nm (F-8837, Life Technologies, Inc.).
(3) 15 μm polystyrene fluorescent beads Ex. 505 nm/Em. 515 nm (F-8844, Life Technologies, Inc.).
(4) 15 μm polystyrene fluorescent beads Ex. 540 nm/Em. 560 nm (F-8841, Life Technologies, Inc.).
(5) 15 μm polystyrene fluorescent beads Ex. 580 nm/Em. 605 nm (F-8842, Life Technologies, Inc.).

The results of the comparative example are shown in FIGS. 19(a-1) and 19(a-2), and the results of the example 3 are shown in FIGS. 19(b-1) and 19(b-2). FIGS. 19(a-1) and 19(b-1) show the entirety of the bright-field image and the fluorescent image, and FIGS. 19(a-2) and 19(b-2) show an enlarged part of the image of FIGS. 19(a-2) and 19(b-1). The numbers 1 through 5 on the image in FIG. 19(b-2) correspond to the fluorescent beads (2) through (5) above and the non-fluorescent beads (1) above. FIGS. 20(1) through 20(5) show the intensity profile on the dotted line traversing the non-fluorescent beads (1) and fluorescent beads (2) through (5) on the image in FIG. 19(b-2). Note that in FIGS. 20(1) through 20(5) the position on the dotted line in FIG. 19(b-2) is the X coordinate.

As shown in FIGS. 19(a-1) and 19(a-2), a bright-field image of the non-fluorescent beads (1) and fluorescent beads (2) through (5) by the photodetector 106 by irradiating ultraviolet light at a peak wavelength λpeak of 405 nm. As shown in FIGS. 19(b-1) and 19(b-2), a fluorescent image of the fluorescent beads (2) through (5) are obtained by the photodetector 106 by irradiating ultraviolet light at a peak wavelength λpeak of 207 nm. A shown in FIGS. 20(1) through 20(5), the fluorescent light given off by the fluorescent beads (2) through (6) is detected by color according to the wavelength via the photodetector 106, and the detection intensity surrounding the fluorescent beads is extremely low. Thus, the fluorescent light detection signal S/N ratio improved and the fluorescent substance was detectable with high detection sensitivity. When using the photodetector 106 of the third embodiment, the bright-field image and plurality of color fluorescent images were both obtained by changing the wavelength of the light source.

Example 4

As shown in FIGS. 21(I) through 21(III), antigen 331 and biotin-conjugated primary antibody 321 captured by streptavidin-conjugated fluorescent magnetic particles 320 are coupled, and secondary antibody 341 labeled by enzyme 3411 is bound to the antigen 331 to produce a complex, and this complex is suspended in a fluorescent substrate solution. The fluorescent substance is produced by reaction between the fluorescent substrate and the enzyme 3411. Specifically, using an automatic pre-processing apparatus, 50 μL of antigen capture antibody solution (HISCL (trademark)-2000i R1 reagent, Sysmex Corp.), and 20 μL of recombinant HBs antigen (HISCL HBsAg, Sysmex Corp.) at OIU/mL or 2500 IU/mL were reacted at 42° C. for 3 minutes. 30 μL of magnetic beads suspension (HISCL-2000i R2 reagent, Sysmex Corp.) was added and reacted at 42° C. for 3 minutes, then subjected to magnetic separation. The antigen capture antibody was captured by the magnetic beads via this reaction as shown in FIG. 20(1).

Thereafter, cleaning by combination of dispensing 300 μL of cleaning liquid and magnetic separation was performed twice. 100 μL of ALP labeling antibody solution (HISCL-2000i R2 reagent, Sysmex Corp.) was added, reacted 42° C. for 3 minutes, then subjected to magnetic separation. The enzyme labeled secondary antibody was coupled to the antigen in this way as shown in FIG. 20(2). Thereafter, cleaning by combination of dispensing 300 μL of cleaning liquid and magnetic separation was performed three times. Then, cleaning by combination of dispensing 150 μL of cleaning liquid and magnetic separation was performed. 50 μL of dispersion liquid (HISCL-2000i R2 reagent, Sysmex Corp.), was subsequently added and mixed. Then, 20 μL of am ALP fluorescent substrate, AttoPhos (trademark) solution (S1000, Promega Corp.) was added and mixed.

Figure 22:
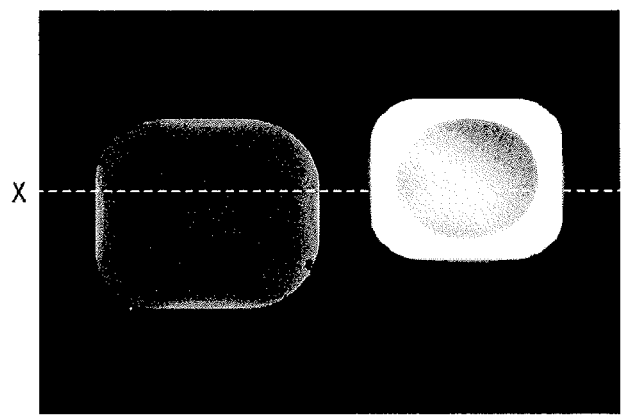
FIG. 22 is an image obtained by example 4.
Figure 23:
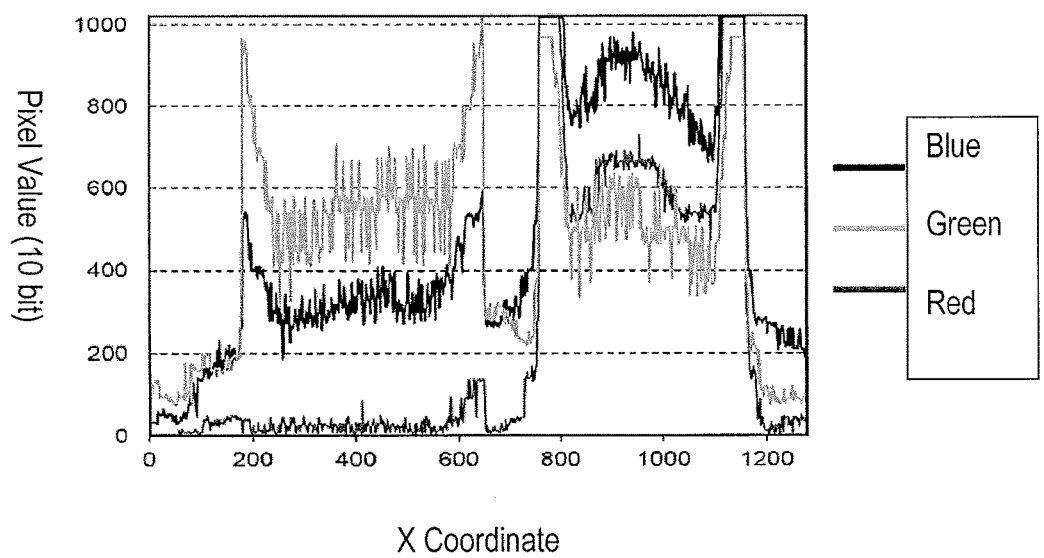
FIG. 23 shows the intensity profile on the X axis in FIG. 22.

The mixed solution reacted with 0 IU/mL recombinant HBs antibody as a negative control, and the mixed solution reacted with 2500 IU/mL recombinant HBs antibody as a positive control were titrated in 2 μL doses on the color CMOS image sensor of photodetector 106 shown in FIG. 10. A fluorescent image was obtained by irradiation with ultraviolet light at a peak wavelength of 270 nm from the LED light source. The fluorescent image is shown in FIG. 22. FIG. 23 shows the intensity profile (pixel value) on the X axis in the fluorescent image of FIG. 22.

As shown in FIGS. 22 and 23, the entire image has low detection intensity due to the small amount of fluorescent substance in the fluorescent image of the negative control. In contrast, since the positive control contains sufficient fluorescent substance produced by reaction between the fluorescent substrate and enzyme label, the detection intensity is higher and a color image is obtained with recognizable colors according to wavelength.

What is claimed is:
1. An analyte detection method for detecting an analyte contained in a biological sample, the method comprising:
(a) irradiating light of a first peak wavelength on a complex containing the analyte and a fluorescent substance which gives off light of a second peak wavelength of 450 nm or higher but not exceeding 900 nm when irradiated with the light of the first peak wavelength of 240 nm or higher but not exceeding 300 nm; and (b) detecting the light of the second peak wavelength given off by the fluorescent substance when irradiated by the light of the first peak wavelength, by a photodetector, wherein the photodetector has a quantum efficiency in the second peak wavelength that is two or more times the quantum efficiency in the first peak wavelength.

2. The analyte detection method of claim 1, wherein the photodetector distinguishes and detects light of a plurality of colors having peak wavelengths in a range from 450 nm but not exceeding 900 nm.

3. The analyte detection method of claim 2, wherein the photodetector comprises:
a light receiving part for receiving light, and
a filter part which transmits part of the light given off by the fluorescent substance and which is arranged between the light receiving part and the fluorescent substance.

4. The analyte detection method of claim 3, wherein the filter part comprises:
a first filter which transmits light in a first wavelength range, a second filter which transmits light in a second wavelength range that differs from the first wavelength range, and a third filter which transmits light in a third wavelength range that differs from the first and second wavelength ranges.

5. The analyte detection method of claim 4, wherein the first filter transmits light of the blue wavelengths, the second filter transmits light of the green wavelengths, and the third filter transmits light of the red wavelengths.

6. The analyte detection method of claim 3, wherein the filter part is an absorption filter.

7. The analyte detection method of claim 1, wherein the photodetector has a quantum efficiency in the first peak wavelength of less than 10%.

8. The analyte detection method of claim 7, wherein the photodetector has a quantum efficiency in the first peak wavelength of less than 5%.

9. The analyte detection method of claim 1, wherein the photodetector comprises a photoelectric conversion element using a silicon substrate.

10. The analyte detection method of claim 9, wherein the photodetector is a micro PMT, PIN photodiode, APD, MPCC, EMCCD, CCD image sensor, CMOS image sensor, or NMOS image sensor.

11. The analyte detection method of claim 10, wherein the photodetector is a micro PMT or CMOS image sensor.

12. The analyte detection method of claim 1, wherein the fluorescent substance are quantum dots or organic dye.

13. The analyte detection method of claim 1, wherein the fluorescent substance and the photodetector are arranged in sequence in the direction of the irradiating light of the first peak wavelength when light of the first peak wavelength is irradiated.

14. The analyte detection method of claim 1, wherein the analyte is a nucleic acid, protein, or peptide.

15. The analyte detection method of claim 1, further comprising a step of (c) forming a complex by binding the fluorescent substance to the analyte.

16. A fluorescence detection method comprising:
(a) irradiating light of a first peak wavelength on a fluorescent substance which gives off light of a second peak wavelength of 450 nm or higher but not exceeding 900 nm when irradiated with light of the first peak wavelength of 240 nm or higher but not exceeding 300 nm; and (b) detecting the light of the second peak wavelength given off by the fluorescent substance when irradiated by light of the first peak wavelength, by a photodetector, wherein the photodetector has a quantum efficiency in the second peak wavelength that is two or more times the quantum efficiency in the first peak wavelength.

17. The method of claim 16, wherein the photodetector distinguishes and detects light of a plurality of colors having peak wavelengths in a range from 450 nm but not exceeding 900 nm.

18. The method of claim 17, wherein the photodetector comprises:
a light receiving part for receiving light, and
a filter part which transmits part of the light given off by the fluorescent substance and which is arranged between the light receiving part and the fluorescent substance.

* * * * *